(12) United States Patent
Parkin et al.

(10) Patent No.: US 7,553,618 B2
(45) Date of Patent: Jun. 30, 2009

(54) METHOD FOR DETERMINING HUMAN IMMUNODEFICICIENCY VIRUS TYPE 1 (HIV-1) HYPERSUSCEPTIBILITY TO THE PROTEASE INHIBITOR AMPRENAVIR

(75) Inventors: Neil T. Parkin, Belmont, CA (US); Ellen Paxinos, San Jose, CA (US); Colombe Chappey, San Francisco, CA (US); Mary T. Wrin, Fremont, CA (US); Andrea Gamarnik, Chandler, AZ (US); Christos J. Petropoulos, Half Moon Bay, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 793 days.

(21) Appl. No.: 10/612,600

(22) Filed: Jul. 1, 2003

(65) Prior Publication Data

US 2004/0106106 A1    Jun. 3, 2004

Related U.S. Application Data

(60) Provisional application No. 60/393,234, filed on Jul. 1, 2002.

(51) Int. Cl.
  *C12Q 1/70*    (2006.01)
  *A61K 39/21*   (2006.01)
(52) U.S. Cl. .................................... 435/5; 424/208.1
(58) Field of Classification Search .................... 435/5; 424/188.1, 208.1
   See application file for complete search history.

(56) References Cited

U.S. PATENT DOCUMENTS

| | | | |
|---|---|---|---|
| 5,436,131 | A | 7/1995 | Condra et al. |
| 5,766,842 | A | 6/1998 | Melnick et al. |
| 5,837,464 | A | 11/1998 | Capon et al. |
| 6,033,902 | A | 3/2000 | Haseltine et al. |
| 6,103,462 | A | 8/2000 | Paulous et al. |
| 6,242,187 | B1 | 6/2001 | Capon et al. |
| 2002/0064838 | A1 | 5/2002 | Parkin et al. |
| 2003/0108857 | A1 | 6/2003 | Parkin et al. |

FOREIGN PATENT DOCUMENTS

| | | |
|---|---|---|
| WO | WO99/67427 | 6/1999 |
| WO | WO00/78996 | 12/2000 |
| WO | WO02/22076 | 3/2002 |
| WO | WO02/068618 | 9/2002 |
| WO | WO02/099387 | 12/2002 |
| WO | WO03/070700 | 8/2003 |
| WO | WO2004/003512 | 1/2004 |
| WO | WO2004/003514 | 1/2004 |

OTHER PUBLICATIONS

Parkin, N. T., et al., 2000, Loss of antiretroviral drug susceptibility at low viral load during early virologic failure in treatment-experienced patients, AIDS 14:2877-2887.*

Ziermann, R., et al., 2000, "A mutation in human immunodeficiency virus type 1 protease, N88S, that causes in vitro hypersensitivity to amprenavir", J. Virol. 74(9):4414-4419.*

Int'l Search Report for PCT/US03/21335, May 3, 2004.

Genbank Accession No. P12497 POL Polyprotein (2004).

Genbank Accession No. AF324493 HIV-1 vector pNL4 . . . [gi:12831134] (2001).

Gervaix, et al., (1997), "A New Reporter Cell Line to Monitor HIV Infection and Drug Susceptibility in Vitro," *Proc. Natl. Acad. Sci. USA*, 94: 4653-4658.

Gunthard, et al., (1998), "Comparative Performance of High-Density Oligonucleotide Sequencing and Dideoxynucleotide Sequencing of HIV Type 1 *pol* From Clinical Samples," *Aids Research and Human Retroviruses*. 14(10):869-876.

Herrmann, et al., (1997), "A Working Hypotheses-Virus Resistance Development As An Indicator of Specific Antiviral Activity," *Ann. NY Acad Sciences*, 284: 632-637.

Hertogs, et al., (1998), "A Rapid Method for Simultaneous Detection of Phenotypic Resistance to Inhibitors of Protease and Reverse Transcriptase in Recombinant Human Immunodeficiency Virus Type 1 Isolates From Patients Treated with Antiretroviral Drugs," *Antimicrobial Agents and Chemotherapy*, 42(2): 269-276.

Hirsch, et al., (2000), "Antiretroviral Drug Resistance Testing in Adult HIV-1 Infection" *JAMA*, 283(18): 2417-26.

Petropoulos, et al., (2000), "A Novel Phenotypic Drug Susceptibility Assay For Human Immunodeficiency Virus Type 1," *Antimicrobial Agents and Chemotherapy*, 44(4): 920-928.

Race, et al., (1999), "Analysis of HIV Cross-Resistance to Protease Inhibitors Using A Rapid Single-Cycle Recombinant Virus Assay For Patients Failing On Combination Therapies," *AIDS*, 13(15): 2061-2068.

Schuurman, et al., (1999), "Worldwide Evaluation of DNA Sequencing Approaches for Identification of Drug Resistance Mutations in the Human Immunodeficiency Virus Type 1 Reverse Transcriptase," *Journal of Clinical Microbiology*, 37(7): 2291-2296.

Shi, et al., (1997), "A Recombinant Retroviral System for Rapid In Vivo Analysis of Human Immunodeficiency Virus Type 1 Susceptibility to reverse Transcriptase Inhibitors," *Antimicrobial Agents and Chemotherapy*, 41(12): 2781-85.

Ziermann, et al.,(2000), "A Mutation in Human Immunodeficiency Virus Type 1 Protease, N88S, That Causes In Vitro Hypersensitivity to Amprenavir," *Journal of Virology*, 74(9): 4414-4419.

Int'l Search Report for PCT/US00/17178, Dec. 2000.

Int'l Search Report for PCT/US01/28754, Mar. 2002.

(Continued)

*Primary Examiner*—Jeffrey S. Parkin
(74) *Attorney, Agent, or Firm*—Jones Day

(57) ABSTRACT

The present invention provides an approach for developing an algorithm for determining the effectiveness of anti-viral drugs based on a comprehensive analysis of paired phenotypic and genotypic data guided by phenotypic clinical cut-offs. In one aspect, the algorithm allows one to provide a patient with effective treatment. It helps predict whether an infected individual will respond to treatment with an anti-viral compound, thereby allowing an effective treatment regimen to be designed without subjecting the patient to unnecessary side effects. Also, by avoiding the administration of ineffective drugs, considerable time and money is saved.

6 Claims, 9 Drawing Sheets

OTHER PUBLICATIONS

Int'l Search Report for PCT/US02/01682, Sep. 2002.
Int'l Search Report for PCT/US02/18684, Jan. 2003.
Int'l Search Report for PCT/US03/04362, Dec. 2004.
Int'l Search Report for PCT/US03/21023, Jul. 2004.
Carrillo et al., (1998), "In Vitro Selection and Characterization of Human Immunodefciency Virus Type 1 Variants With Increased Resistance to ABT-378, a Novel Protease Inhibitor," *Journal of Virology*, 72(9): 7532-41.
Condra et al., (1996), "Genetic Correlates of In Vivo Resistance to Indinavir, a Human Immunodeficiency Virus Type 1 Protease Inhibitor," *Journal of Virology*, 70(12): 8270-76.
Craig et al., 1998 "HIV Protease Genotype and Viral Sensitivity to HIV Protease Inhibitors Following Saquinavir Therapy", *AIDS*, 12: 1611-1618.
Dreyer GB, et al."A Symmetric Inhibitor Binds HIV-I Protease Asymmetrically" *Biochemistry* (1993) 32:937-947.
J. Eron, et al., (1995) Preliminary Assessment of 141 W94 in Combination with Other Protease Inhibitors, *5th Conference on Retroviruses and Opportunistic Infections*.
Gong et al., (2000), "In Vitro Resistance Profile of the Human Immunodeficiency Virus Type 1 Protease Inhibitor BMS-232632," *Antimicrobial Agents and Chemotherapy*, 44(9): 2319-26.
Hill, A. et al. (1998) "Low frequency of genotypic mutations associated with resistance to AZT and 3TC after combination treatment with indinavar," *Int. Conf. AIDS* 12:812, (Abstract No. 6).
Katzenstein et al., (2002), "Baseline Phenotypic Susceptibility and Virologic failure over 144 weeks Among Nucleoside RT Inhibitor Experienced Subjects in ACTG 364," Antiretroviral Drug Resistance Testing in Adult HIV-1 Infection," *2002 9th Conference on Retroviruses and Opportunistic Infections*, Session 77 Poster Session 591-T.
Katzenstein et al., (2002), "The Inhibitory Quotient (IQ) for Saquinavir (SQV) Predicts Virologic Response to Salvage Therapy," *2002 9th Conference on Retroviruses and Opportunistic Infections*, Session 28 Poster Session 129.
Kempf et al., (2001), "Identification of Genotypic Changes in Human Immunodeficiency Virus Protease that Correlate With Reduced Susceptibility to the Protease Inhibitor Lopinavir Among Viral Isolates From Protease Inhibitor-Experienced Patients," *Journal of Virology*, 75(16): 7462-69.
Kim, (1995) "Crystal Structure of HIV-1 Protease in Complex with VX-478, a Potent and Orally Bioavailable Inhibitor of the Enzyme," *J. Am. Chem. Soc.*, 117: 1181-1182.
Lambert DM, et al. (1992) "Human Immunodeficiency Virus Type 1 Protease Inhibitors Irreversibly Block Infectivity of Purified Virions From Chronically Infected Cells" *Anit Microb Agents Chem* 36:982-98.
Larder, et al., (1995) "Potential Mechanism for; Sustained Antiretroviral Efficacy of AZT-3TC Combination Therapy," *Science*, 269; 696-699.
Lazdins, et al., (1997) "In Vitro Effect of al-Acid Glycoprotein on the Anti-Human Immunodeficiency Virus (HIV) Activity of the Inhibitor CGP 61775: A Comparative Study wits Other Relevant HIV Protease Inhibitors," *J Infec. Dis.*, 175: 1063-1070.
Livingston, et al., (1995) "Weak Binding of VX-478 tc Human Plasma Proteins and Implications for Anti-Humar Immunodeficiency Virus Therapy," *J Infec. Dis.*, 172:1.238-124.
Maguire et al., (2002), "Emergence of Resistance to Protease Inhibitor Amprenavir in Human Immunodeficiency Virus Type 1-Infected Patients: Selection of Four Alternative Viral Protease Genotypes and Influence of Viral Susceptibility to Coadministered Reverse Transcriptase Nucleoside Inhibitors," *Antimicrobial Agents and Chemotherapy*, 46(3): 731-738.
Mahalingam, et al., (1999) "Structural and Kinetic Analysis of Drug Resistant Mutants of HIV Protease," *Biochem.*, 263: 1-9.
Miller M, et al. (1989) Structure of Complex of Synthetic HIV-1j Protease with a SubstrateBased Inhibitor at 2.3 A Resolution, *Science* 246:1149-1152.

Mohri H, et al. (1993) "Quantitation of Zidovudine-Resistant Human Immunodeficiency Virus Type 1 in the Blood of Treated and Untreated Patients," *PNAS* 90:25-29.
Murphy, et al., (1999) "Treatment with Amprenavir Alone or Amprenavir with Zidovudine and Lamivudine in Adults with Human Immunodeficiency Virus Infection" *J. Infec. Dis.*, 179: 808-81 E.
Najera I, et al. (1994) "Natural Occurrence of Drug ResistancE Mutations in the Reverse Transcriptase of Human Immunodeficiency Virus Type 1 Isolates," *Aids Res Hum Retroviruses* 10:1479-1488.
Najera I, et al. (1995) "pol Gene Quasispecies of Humar Immunodeficiency Virus: Mutations Associated with Drug ResistancE in Virus From Patients Undergoing No Drug Therapy," *J Virol* 69:23-31.
Palmer, et al., (1999) "Highly Drug-resistant HIV-1 Clinical Isolates Are Cross-resistant to Many Antiretroviral Compounds in Current Clinical Development," *AIDS*, 13: 661-667.
Parkin, et al., (1999) "Phenotypic changes in Drug Susceptibility Associated with Failure of Human Immunodeficiency Virus Type 1 (HIV-1) Triple Combination Therapy," *J Infec. Dis.*, 180: 865-870.
Partaledis, et al., (1995) "In Vitro Selection and Characterization of Human Immunodeficiency Virus Type 1 (HIV-1) Isolates with Reduced Sensitivity to Hydroxyethylamino Sulfonamide Inhibitors of HIV-1 Aspartyl Protease," *Journal of Virology*, 69: 5228-5235.
Patick, et al., (1998) "Genotypic and Pheno typic Characterization of Human Immunodeficiency Virus Type 1 Variants Isolated from Patients Treated with the Protease Inhibitor Nelfinavir," *Antimicrobial Agents and Chemotherapy*, 42(10): 2637-44.
Petit SC, et al. (1993) "The Specificity of the HIV-1 Protease" *Drug Discov Des* 1:69-83.
Roberts NA, et al. (1990) "Rational Design of Peptide-Based HIV Proteinase" *Science* 248:358361.
Roberts, N. A., (1995) "Drug-resistance patterns of saquinavir and other HIV proteinase inhibitors," *AIDS.9* (supp 2) S27-S32.
Rusconi, Stefano. et al. (2000): "Susceptibility to PNU-140690 (Tipranavir) of Human Immunodeficiency Virus Type 1 Isolates Derived From Patients with Multidrug Resistance to Other Protease Inhibitors," *Antimicrobial Agents and Chemotherapy*, 44(5): 1328-32.
Sadler, et al., (1999) "Safety and Pharmacokinetics of Amprenavir (141 W94), a Human Immunodeficiency Virus (HIV) Type 1 Protease Inhibitor, Following Oral Administration of Single Doses to HIV-Infected Adults," *Antimicrobial Agents and Chemotherapy*, 43: 1686-1692.
Sarkar, et al., (1990) "The "Megaprimer" Method of Site-Directed Mutagenesis," *BioTech* 8(4):404-407.
Tian, et al., (1998) "Zidovudine/Lamivudine Co-resistance Is Preceded by a Transient Period of Zidovudine Hypersensitivity," 2nd International Workshop on HIV Drug Resistance and Treatment Strategies, Abstract 30.
Tisdale, M. et al. (1995): "Cross-Resistance Analysis of Human Immunodeficiency Virus Type 1 Variants Individually Selected for Resistance to Five Different Protease Inhibitors," *Antimicrobial Agents and Chemotherapy* 39(8):1704-10.
Tisdale, M. et al. (1998): "Genotypic and phenotypic analysis of HIV from patients on ZDV/3TC/amprenavir combination therapy," *Int. Conf AIDS* 12:583 (Abstract No. 32312).
Tucker, et al., (1998) "Estimate of the Frequency of Human Immunodeficiency Virus Type 1 Protease Inhibitor Resistance Within Unselected Virus Populations In Vitro," *Antimicrobial Agents and Chemotherapy*, 42: 478-480.
Young et al. J. Infect. Disease 178(5) 1497-1501 (1998).
Andrew Chin, Mar. 14, 2002 "On the Preparation and Utilization of Isolated and Purified Oligonucleotides," Produced on Mar. 9, 2002 and contributed to the Public Collection of the Katherine R. Everett Law Library of the University of North Carolina. (Electronic Copy provided on CD-Rom).

\* cited by examiner

Figure 9A

SEQ. ID. NO: 1: NL4-3 HIV Protease Amino Acid Sequence
PQITLWQRPL VTIKIGGQLK EALLDTGADD TVLEEMNLPG RWKPKMIGGI
GGFIKVRQYD QILIEICGHK AIGTVLVGPT PVNIIGRNLL TQIGCTLNF

Figure 9B

SEQ. ID. NO: 2: NL4-3 HIV Protease Gene Nucleotide Sequence

| | |
|---|---|
| 1-10 | CCT CAG ATC ACT CTT TGG CAG CGA CCC CTC |
| 11-20 | GTC ACA ATA AAG ATA GGG GGG CAA TTA AAG |
| 21-30 | GAA GCT CTA TTA GAT ACA GGA GCA GAT GAT |
| 31-40 | ACA GTA TTA GAA GAA ATG AAT TTG CCA GGA |
| 41-50 | AGA TGG AAA CCA AAA ATG ATA GGG GGA ATT |
| 51-60 | GGA GGT TTT ATC AAA GTA AGA CAG TAT GAT |
| 61-70 | CAG ATA CTC ATA GAA ATC TGC GGA CAT AAA |
| 71-80 | GCT ATA GGT ACA GTA TTA GTA GGA CCT ACA |
| 81-90 | CCT GTC AAC ATA ATT GGA AGA AAT CTG TTG |
| 91-99 | ACT CAG ATT GGC TGC ACT TTA AAT TTT |

METHOD FOR DETERMINING HUMAN IMMUNODEFICICIENCY VIRUS TYPE 1 (HIV-1) HYPERSUSCEPTIBILITY TO THE PROTEASE INHIBITOR AMPRENAVIR

This application is entitled to and claims priority to U.S. Provisional Application No. 60/393,234, filed Jul. 1, 2002, the contents of which is hereby incorporated by reference in its entirety.

1. FIELD OF INVENTION

This invention relates to compositions and methods for determining the susceptibility of a pathogenic virus to an anti-viral compound. The compositions and methods are useful for identifying effective drug regimens for the treatment of viral infections, and identifying and determining the biological effectiveness of potential therapeutic compounds.

2. BACKGROUND OF THE INVENTION

More than 60 million people have been infected with the human immunodeficiency virus ("HIV"), the causative agent of acquired immune deficiency syndrome ("AIDS"), since the early 1980s. See Lucas, 2002, *Lepr Rev.* 73(1):64-71. HIV/AIDS is now the leading cause of death in sub-Saharan Africa, and is the fourth biggest killer worldwide. At the end of 2001, an estimated 40 million people were living with HIV globally. See Norris, 2002, *Radiol Technol.* 73(4):339-363.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors such as AZT, ddI, ddC, d4T, 3TC, abacavir, nucleotide reverse transcriptase inhibitors such as tenofovir, non-nucleoside reverse transcriptase inhibitors such as nevirapine, efavirenz, delavirdine and protease inhibitors such as saquinavir, ritonavir, indinavir, nelfinavir, amprenavir and lopinavir.

One consequence of the action of an anti-viral drug is that it can exert sufficient selective pressure on virus replication to select for drug-resistant mutants (Herrmann et al., 1977, *Ann NY Acad Sci* 284:632-637). With increasing drug exposure, the selective pressure on the replicating virus population increases to promote the more rapid emergence of drug resistant mutants.

With the inevitable emergence of drug resistance, strategies must be designed to optimize treatment in the face of resistant virus populations. Ascertaining the contribution of drug resistance to drug failure is difficult because patients that are likely to develop drug resistance are also likely to have other factors that predispose them to a poor prognosis (Richman, 1994, *AIDS Res Hum Retroviruses* 10:901-905). In addition, each patient typically harbors a diverse mixture of mutant strains of the virus with different mutant strains having different susceptibilities to anti-viral drugs.

The traditional tools available to assess anti-viral drug resistance are inadequate; the classical tests for determining the resistance of HIV to an anti-viral agent are complex, time-consuming, expensive, potentially hazardous and not custom tailored to the treatment of a given patient. See Barre-Sinoussi et al., 1983, *Science* 220:868-871; Popovic et al., 1984, *Science* 224:497-500), and variations of it (see, e.g., Goedert et al., 1987, *JAMA* 257:331-334; Allain et al., 1987, *N. Engl. J Med.* 317:1114-1121; Piatak et al., 1993, *Science* 259:1749-1754; Urdea, 1993, *Clin. Chem.* 39:725-726; Kellam and Larder, 1994, *Antimicrobial Agents and Chemo.* 38:23-30.

Two general approaches are now used for measuring resistance to anti-viral drugs. The first, called phenotypic testing, directly measures the susceptibility of virus taken from an infected person's virus to particular anti-viral drugs. Petropoulos et al., 2000, *Antimicrob. Agents Chemother.* 44:920-928 and Hertogs et al., 1998, *Antimicrob Agents Chemother* 42(2):269-76 provide a description of phenotypic assays in widespread use today. Gunthard et al., 1998, *AIDSRes Hum Retroviruses* 14:869-76 and Schuurman et al., 1999, *J Clin Microbiol.* 37:2291-96 discuss currently prevalent genotypic assays. Hirsch et al., 2000, *JAMA* 283:2417-26 provide a general analysis of the currently available assays for testing drug susceptibility.

The second method, called genotypic testing, detects mutations in the virus that affect drug susceptibility and can associate specific genetic mutations with drug resistance and drug failure. Genotypic testing examines virus taken from a patient, looking for the presence of specific genetic mutations that are associated with resistance to certain drugs. Genotypic testing has a few advantages over phenotypic testing, most notably the relative simplicity and speed with which the test can be performed. The testing can take as little as a few days to complete, and because it is less complex, it is somewhat cheaper to perform. However, interpretation of genotypic data is dependent on previous knowledge of the relationships between specific mutations and changes in drug susceptibility.

Efforts to date to use genotypic correlates of reduced susceptibility to predict the effectiveness of anti-viral drugs, especially drugs targeted against the ever-evolving HIV are, at best, imperfect. An algorithm that can more accurately predict whether a given anti-viral drug or combination of drugs would be effective in treating a given patient would save time and money by identifying drugs that are not likely to succeed before they are administered to the patient. More importantly, it would improve the quality of life of the patient by sparing him or her the trauma of treatment with potent toxins that result in no improvement with respect to his or her HIV infection. Therefore, an urgent need exists for a more accurate algorithm for predicting whether a particular drug would be effective for treating a particular patient. Moreover, a genotype based assay can be faster and more cost effective than phenotypic assays.

3. SUMMARY OF THE INVENTION

The present invention provides methods and compositions for developing and using algorithms for determining the effectiveness of an anti-viral therapy or combination of therapies. The algorithms are based on an analysis of paired phenotypic and genotypic data guided by phenotypic clinical cut-offs (the point at which resistance to a therapy begins and sensitivity ends). The algorithms significantly improve the quality of life of a patient by accurately predicting whether a given anti-viral drug would be effective in treating the patient, thereby sparing him or her the trauma of treatment with potent toxins that result in no improvement in his or her HIV infection.

In one aspect, the present invention provides methods for determining the susceptibility of a virus to an anti-viral treatment, comprising detecting, in the viral genome or viral enzymes, the presence or absence of mutations associated with hypersusceptibility to the anti-viral treatment.

In another aspect, the present invention provides methods for determining the effectiveness of an anti-viral treatment of an individual infected with a virus, comprising: detecting, in a sample from said individual, the presence or absence of mutations associated with hypersusceptibility to the anti-viral treatment.

The present invention also provides methods of monitoring the clinical progression of viral infection in individuals receiving an anti-viral treatment by determining, as described above, the effectiveness of the same or a different anti-viral treatment. In one embodiment, the present invention provides nucleic acids and polypeptides comprising a mutation in the protease of a human immunodeficiency virus ("HIV") associated with hypersusceptibility to a protease inhibitor. Examples of protease inhibitors include, but are not limited to, saquinavir, ritonavir, indinavir, nelfinavir, amprenavir and lopinavir.

In another aspect, the invention provides a method for determining whether a HIV has an increased likelihood of being hypersusceptible to treatment with a protease inhibitor, comprising: detecting whether the protease encoded by said HIV exhibits the presence or absence of a mutation associated with hypersusceptibility to treatment with said protease inhibitor at amino acid position 16, 20, 33, 36, 37, 39, 45, 65, 69, 77, 89 or 93 of an amino acid sequence of said protease, wherein the presence of said mutation indicates that the HIV has an increased likelihood of being hypersusceptible to treatment with the protease inhibitor, with the proviso that said mutation is not L33F.

In another aspect, the invention provides a method of determining whether an individual infected with HIV has an increased likelihood of being hypersusceptible to treatment with a protease inhibitor, comprising: detecting, in a sample from said individual, the presence or absence of a mutation associated with hypersusceptibility to treatment with said protease inhibitor at amino acid position 16, 20, 33, 36, 37, 39, 45, 65, 69, 77, 89 or 93 of the amino acid sequence of the protease of the HIV, wherein the presence of said mutation indicates that the individual has an increased likelihood of being hypersusceptible to treatment with the protease inhibitor, with the proviso that said mutation is not L33F.

In another preferred embodiment, the human immunodeficiency virus is human immunodeficiency virus type 1 ("HIV-1").

In another aspect, the invention provides an oligonucleotide between about 10 and about 40 nucleotides long encoding a portion of an HIV protease that comprises a mutation at amino acid position 16, 20, 33, 36, 37, 39, 45, 65, 69, 77, 89 or 93 of an amino acid sequence of said protease in said human immunodeficiency virus, wherein the mutation is associated with hypersusceptibility to a protease inhibitor, with the proviso that said mutation is not L33F.

In another embodiment, the invention provides an isolated polypeptide that comprises at least ten contiguous residues of the amino acid sequence of SEQ ID NO:1, wherein the polypeptide comprises at least one mutation of the invention listed above, and wherein the mutation is associated with hypersusceptibility to a protease inhibitor.

In another embodiment, the polypeptide comprising said mutation or mutations is at least 70%, but less than 100%, identical to a polypeptide having the amino acid sequence of SEQ ID NO:1; the polypeptide has an amino acid sequence that is greater than 80% identical to the amino acid sequence of SEQ ID NO:1; or the polypeptide has an amino acid sequence that is greater than 90% identical to the amino acid sequence of SEQ ID NO:1; wherein the mutation is associated with hypersusceptibility to a protease inhibitor.

In one embodiment, the invention provides a method wherein the presence or absence of a mutation in a protease is detected by hybridization with a sequence-specific oligonucleotide probe to a nucleic acid sequence of human immunodeficiency virus encoding said mutation, wherein the occurrence of hybridization indicates said presence or absence of said mutation.

In another embodiment, the invention provides a method wherein the presence or absence of a mutation in a protease is detected by determining a nucleic acid sequence encoding said mutation.

In another embodiment, the invention provides a method wherein the presence or absence of a mutation in a protease is detected by amplifying the nucleic acid by, for example, polymerase chain reaction.

In one embodiment, the individual is undergoing or has undergone prior treatment with an anti-viral drug. In another embodiment, the anti-viral drug is said or different protease inhibitor.

In another aspect, the invention provides a method for detecting the presence or absence of a mutation associated with hypersusceptibility to treatment with said protease inhibitor at at least 2, 3, 4, 5, 6, 7, 8, 9, 10, 11 or 12 of the amino acid positions.

In another aspect, the invention provides a method for determining whether a HIV, e.g., HIV-1, has a decreased likelihood of being hypersusceptible to a protease inhibitor, comprising: detecting whether the protease encoded by said HIV-1 exhibits the presence or absence of a mutation negatively associated with hypersusceptibility to said protease inhibitor at amino acid position 10, 15, 36, 41, 57, 60, 63, 71 or 93 of an amino acid sequence of said protease, wherein the presence of said mutation indicates that the HIV has a decreased likelihood of being hypersusceptible to the protease inhibitor.

In another aspect, the invention provides a method for determining whether an individual infected with HIV, e.g., HIV-1, has a decreased likelihood of being hypersusceptible to treatment with a protease inhibitor, comprising detecting, in a sample from said individual, the presence or absence of a mutation negatively associated with hypersusceptibility to treatment with said protease inhibitor at amino acid position 10, 15, 36, 41, 57, 60, 63, 71 or 93 of the amino acid sequence of the protease of the HIV-1, wherein the presence of said mutation indicates that the individual has a decreased likelihood of being hypersusceptible to treatment with the protease inhibitor.

4. BRIEF DESCRIPTION OF THE FIGURES

Figure 1:
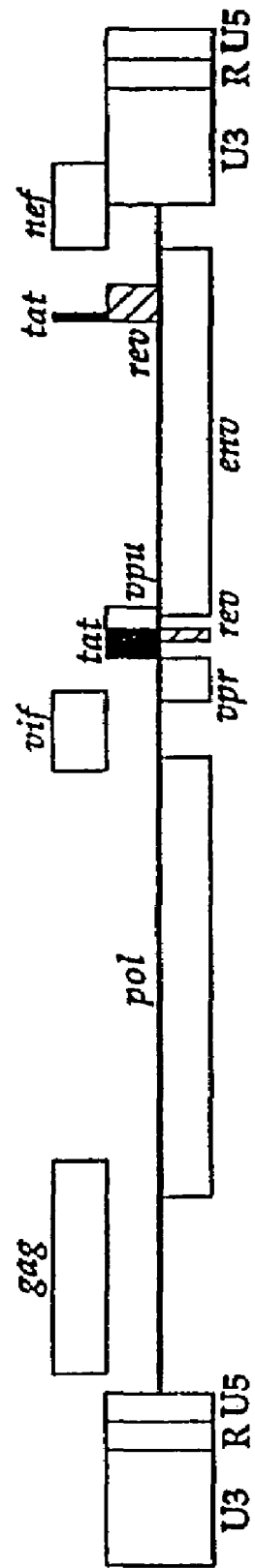
FIG. 1 is a diagrammatic representation of the genomic structure of HIV-1.

FIG. 9A shows the amino acid sequence of the NL4-3 HIV (GenBank Accession No. P12497) protease (SEQ. ID. NO: 1).

FIG. 9B shows the nucleic acid sequence for the NL4-3 HIV (GenBank Accession No. AF324493) protease gene (SEQ. ID. NO: 2).

5. DETAILED DESCRIPTION OF THE INVENTION

The present invention provides methods and compositions for developing an algorithm for determining the effectiveness of anti-viral drugs based on a comprehensive analysis of paired phenotypic and genotypic data guided by phenotypic clinical cut-offs. The present invention also provides methods for determining the susceptibility of a virus to an anti-viral treatment, methods for determining the effectiveness of an anti-viral treatment of an individual infected with a virus, and methods of monitoring the clinical progression of viral infection in individuals receiving anti-viral treatment. In another aspect, the present invention also provides nucleic acids and polypeptides comprising a mutation in the protease of a human immunodeficiency virus ("HIV") associated with hypersusceptibility to a protease inhibitor.

5.1 Abbreviations

"APV" is an abbreviation for the protease inhibitor amprenavir.

"IDV" is an abbreviation for the protease inhibitor indinavir.

"LPV" is an abbreviation for the protease inhibitor lopinavir.

"NFV" is an abbreviation for the protease inhibitor nelfinavir.

"RTV" is an abbreviation for the protease inhibitor ritonavir.

"SQV" is an abbreviation for the protease inhibitor saquinavir.

"PI" is an abbreviation for protease inhibitor.

"PT-HS" is an abbreviation for "phenotypically hypersusceptible."

"GT-HS" is an abbreviation for "genotypically hypersusceptible."

"PCR" is an abbreviation for "polymerase chain reaction."

"FC" is an abbreviation for "fold change."

"RC" is an abbreviation for "replication capacity"

The amino acid notations used herein for the twenty genetically encoded L-amino acids are conventional and are as follows:

| Amino Acid | One-Letter Abbreviation | Three Letter Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |

-continued

| Amino Acid | One-Letter Abbreviation | Three Letter Abbreviation |
|---|---|---|
| Tyrosine | Y | Tyr |
| Valine | V | Val |

Unless noted otherwise, when polypeptide sequences are presented as a series of one-letter and/or three-letter abbreviations, the sequences are presented in the N→C direction, in accordance with common practice.

Individual amino acids in a sequence are represented herein as AN, wherein A is the standard one letter symbol for the amino acid in the sequence, and N is the position in the sequence. Mutations are represented herein as $A_1NA_2$, wherein $A_1$ is the standard one letter symbol for the amino acid in the reference protein sequence, $A_2$ is the standard one letter symbol for the amino acid in the mutated protein sequence, and N is the position in the amino acid sequence. For example, a G25M mutation represents a change from glycine to methionine at amino acid position 25. Mutations may also be represented herein as $NA_2$, wherein N is the position in the amino acid sequence and $A_2$ is the standard one letter symbol for the amino acid in the mutated protein sequence (e.g., 25M, for a change from the wild-type amino acid to methionine at amino acid position 25). Additionally, mutations may also be represented herein as $A_1N$, wherein $A_1$ is the standard one letter symbol for the amino acid in the reference protein sequence and N is the position in the amino acid sequence (e.g., G25 represents a change from glycine to any amino acid at amino acid position 25). This notation is typically used when the amino acid in the mutated protein sequence is either not known or, if the amino acid in the mutated protein sequence could be any amino acid, except that found in the reference protein sequence. The amino acid positions are numbered based on the full-length sequence of the protein from which the region encompassing the mutation is derived. Representations of nucleotides and point mutations in DNA sequences are analogous.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Unless specified otherwise, single-stranded nucleic acid sequences that are represented as a series of one-letter abbreviations, and the top strand of double-stranded sequences, are presented in the 5'→3' direction.

5.2 Definitions

As used herein, the following terms shall have the following meanings:

Unless otherwise specified, "primaryy mutation" refers to a mutation that affects the enzyme active site, i.e. at those amino acid positions that are involved in the enzyme-substrate complex, or that reproducibly appears in an early round of replication when a virus is subject to the selective pressure of an anti-viral agent, or, that has a large effect on phenotypic susceptibility to an anti-viral agent.

"Secondary Mutation" refers to a mutation that is not a primary mutation and that contributes to reduced susceptibility or compensates for gross defects imposed by a primary mutation.

A "phenotypic assay" is a test that measures the sensitivity of a virus (such as HIV) to a specific anti-viral agent.

A "genotypic assay" is a test that determines a genetic sequence of an organism, a part of an organism, a gene or a part of a gene. Such assays are frequently performed in HIV to establish whether certain mutations are associated with drug resistance are present.

As used herein, "genotypic data" are data about the genotype of, for example, a virus. Examples of genotypic data include, but are not limited to, the nucleotide or amino acid sequence of a virus, a part of a virus, a viral gene, a part of a viral gene, or the identity of one or more nucleotides or amino acid residues in a viral nucleic acid or protein.

"Susceptibilit" refers to a virus' response to a particular drug. A virus that has decreased or reduced susceptibility to a drug has an increased resistance or decreased sensitivity to the drug. A virus that has increased or enhanced or greater susceptibility to a drug has an increased sensitivity or decreased resistance to the drug.

Phenotypic susceptibility of a virus to a given drug is a continuum. Nonetheless, it is practically useful to define a threshold or thresholds to simplify interpretation of a particular fold-change result. For drugs where sufficient clinical outcome data have been gathered, it is possible to define a "clinical cutoff value," as below.

"Hypersusceptibility" ("HS") refers to an enhanced or greater susceptibility to a drug, an increased sensitivity to a drug or decreased resistance to a drug. Hypersusceptibility is defined as a fold change ("FC") (see below) equal to or less than the $10^{th}$ percentile for each protease inhibitors' fold change distribution.

"Clinical Cutoff Value" refers to a specific point at which resistance begins and sensitivity ends. It is defined by the drug susceptibility level at which a patient's probability of treatment failure with a particular drug significantly increases. The cutoff value is different for different anti-viral agents, as determined in clinical studies. Clinical cutoff values are determined in clinical trials by evaluating resistance and outcomes data. Drug susceptibility (phenotypic) is measured at treatment initiation. Treatment response, such as change in viral load, is monitored at predetermined time points through the course of the treatment. The drug susceptibility is correlated with treatment response and the clinical cutoff value is determined by resistance levels associated with treatment failure (statistical analysis of overall trial results).

"$IC_n$" refers to Inhibitory Concentration. It is the concentration of drug in the patient's blood or in vitro needed to suppress the reproduction of a disease-causing microorganism (such as HIV) by n %. Thus, "$IC_{50}$" refers to the concentration of an anti-viral agent at which virus replication is inhibited by 50% of the level observed in the absence of the drug. "Patient $IC_{50}$", refers to the drug concentration required to inhibit replication of the virus from a patient by 50% and "reference $IC_{50}$" refers to the drug concentration required to inhibit replication of a reference or wild-type virus by 50%. Similarly, "$IC_{90}$" refers to the concentration of an anti-viral agent at which 90% of virus replication is inhibited.

A "fold change" is a numeric comparison of the drug susceptibility of a patient virus and a drug-sensitive reference virus. It is the ratio of the Patient $IC_{50}$ to the drug-sensitive reference $IC_{50}$, i.e., Patient $IC_{50}$/Reference $IC_{50}$=Fold Change ("FC"). A fold change of 1.0 indicates that the patient virus exhibits the same degree of drug susceptibility as the drug-sensitive reference virus. A fold change less than 1 indicates the patient virus is more sensitive than the drug-sensitive reference virus. A fold change greater than 1 indicates the patient virus is less susceptible than the drug-sensitive reference virus. A fold change equal to or greater than the clinical cutoff value means the patient virus has a lower probability of response to that drug. A fold change less than the clinical cutoff value means the patient virus is sensitive to that drug.

A virus is "sensitive" to APV, IDV, NFV, SQV and RTV if it has an APV, IDV, NFV, SQV and RTV, respectively, fold change of less than 2.5. A virus is sensitive to LPV if it has an LPV fold change of less than 10.

A virus is "resistant" to APV, IDV, NFV, SQV and RTV if it has an APV, IDV, NFV, SQV and RTV, respectively, fold change of 2.5 or more. A virus is resistant to LPV if it has an LPV fold change of 10 or more.

A virus has an "increased likelihood of being hypersusceptible" to an anti-viral treatment if the virus has a property, for example, a mutation, that is correlated with hypersusceptibility to the anti-viral treatment. A property of a virus is correlated with hypersusceptibility if a population of viruses having the property is, on average, more susceptible to the anti-viral treatment than an otherwise similar population of viruses lacking the property. Thus, the correlation between the presence of the property and hypersusceptibility need not be absolute, nor is there a requirement that the property is necessary (i.e., that the property plays a causal role in increasing susceptibility) or sufficient (i.e., that the presence of the property alone is sufficient) for conferring hypersusceptibility.

A virus has an "decreased likelihood of being hypersusceptible" to an anti-viral treatment if there is a negative correlation which is statistically significant ($P<0.05$) in at least one of the following statistical tests: the t-test for comparison of means, the non-parametric Kruskal-Wallis test or the Fisher's Exact test.

The term "% sequence homology" is used interchangeably herein with the terms "% homology," "% sequence identity" and "% identity" and refers to the level of amino acid sequence identity between two or more peptide sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 60, 70, 80, 85, 90, 95, 98% or more sequence identity to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at http://www.ncbi.nlm.nih.gov/BLAST/. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Altschul, et al., 1997.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Ala (A), Gly (G), Ile (1), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et aL, 1984, *J. Mol. Biol.* 179:125-142. Genetically encoded hydrophobic amino acids include Ala (A), Gly (G), Ile (1), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than7. Basic amino acids typically have positively charged side chains at physiological pH due to association with hydronium ion. Genetically encoded basic amino acids include Arg (R), His (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease or reverse transcriptase is the protease or reverse transcriptase coding sequence, respectively, present in NL4-3 HIV (GenBank Accession No. AF324493). Likewise, the reference protease or reverse transcriptase polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, *Methods in Enzymology* 65:499), dideoxy sequencing (Sanger et al., 1977, *Proc. Natl. Acad. Sci. USA* 74:5463) or hybridization-based approaches (see e.g., Sambrook et al., 2001, *Molecular Cloning: A Laboratory Manual, Cold Spring Harbor Laboratory,* 3$^{rd}$ ed., NY; and Ausubel et al., 1989, *Current Protocols in Molecular Biology, Greene Publishing Associates and Wiley Interscience, NY).*

A "resistance-associated mutation" ("RAM") in a virus is a mutation correlated with reduced susceptibility of the virus to anti-viral agents. A RAM can be found in any one of several viruses, including, but not limited to a human immunodeficiency virus ("HIV"). Such mutations can be found in one or more of the viral proteins, for example, in the protease, integrase, envelope or reverse transcriptase of HIV. A RAM is defined relative to a reference strain. For embodiments of the invention comprising HIV protease, the reference protease is the protease encoded by NL4-3 HIV (GenBank Accession No. AF324493).

A "hypersusceptibility-associated mutation" ("HSAM") in a virus is a mutation correlated with hypersusceptibility of the virus to anti-viral agents. A HSAM can be found in any one of several viruses, including, but not limited to a human immunodeficiency virus ("HIV"). Such mutations can be found in one or more of the viral proteins, for example, in the protease, integrase, envelope or reverse transcriptase of HIV. A HSAM is defined relative to a reference strain. For embodiments of the invention comprising HIV protease, the reference protease is the protease encoded by NL4-3 HIV (GenBank Accession No. AF324493).

A "mutant" is a virus, gene or protein having a sequence that has one or more changes relative to a reference virus, gene or protein.

The terms "peptide," "polypeptide" and "protein" are used interchangeably throughout.

The terms "reference" and "wild-type" are used interchangeably throughout.

The terms "polynucleotide," "oligonucleotide" and "nucleic acid" are used interchangeably throughout.

5.3 Hypersusceptibility-Associated Mutations

In one aspect, the present invention provides nucleic acids and polypeptides comprising a mutation in the protease of HIV. Preferably, the HIV is human immunodeficiency virus type 1 ("HIV-1"). In one embodiment, the mutation is associated with hypersusceptibility to a protease inhibitor. The protease inhibitor can be any protease inhibitor known to one of skill in the art. Examples of protease inhibitors include, but are not limited to, saquinavir, ritonavir, indinavir, nelfinavir, amprenavir and lopinavir.

In one aspect, the present invention provides peptides, polypeptides or proteins comprising a mutation in the protease of HIV associated with hypersusceptibility to a protease inhibitor. In one embodiment, the invention provides a polypeptide derived from the HIV protease and comprising a mutation associated with hypersusceptibility to a protease inhibitor. In another embodiment, the polypeptide comprises more than one mutation associated with hypersusceptibility to a protease inhibitor. Polypeptides of the invention include peptides, polypeptides and proteins that are modified or derived from these polypeptides. In one embodiment, the polypeptide comprises post-translational modifications. In another embodiment, the polypeptide comprises one or more amino acid analogs.

In a preferred embodiment, the polypeptide comprises one or more mutations associated with hypersusceptibility to one or more protease inhibitors. Table 1 provides a list of mutations associated with hypersusceptibility to protease inhibitors.

In another preferred embodiment, the invention provides a polypeptide derived from the HIV protease and comprising at least one mutation at an amino acid position selected from a group consisting of: 16, 20, 33, 36, 37, 39, 45, 65, 69, 77, 89 and 93. In one embodiment, the amino acid at position 33 is not F.

In another preferred embodiment, the polypeptide comprising said mutation comprises at least 10, 15, 20, 25, 30, 35, 40, 45, 50, 60, 70, 80, 85, 90 or 95 contiguous amino acids of SEQ ID NO: 1, within which sequence said mutation or mutations can be present.

In another embodiment, the polypeptide comprising said mutation or mutations is at least 70%, but less than 100%, identical to a polypeptide having the amino acid sequence of SEQ ID NO:1; the polypeptide has an amino acid sequence that is greater than 80% identical to the amino acid sequence of SEQ ID NO:1; or the polypeptide has an amino acid sequence that is greater than 90% identical to the amino acid sequence of SEQ ID NO:1; wherein the mutation is associated with hypersusceptibility to a protease inhibitor.

In one embodiment, said polypeptide is naturally-occurring. In another embodiment, said polypeptide is artificially designed.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (% identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search that detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov.

Another preferred, non-limiting example of a mathematical algorithm utilized for the comparison of sequences is the algorithm of Myers and Miller, CABIOS (1989). Such an algorithm is incorporated into the ALIGN program (version 2.0) that is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.*, 10:3-5; and FASTA described in Pearson and Lipman (1988) *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined ktup can be set to 2 or 1 for protein sequences, or from 1 to 6 for DNA sequences. The default if ktup is not specified is 2 for proteins and 6 for DNA.

The percent identity between two sequences can be determined using techniques similar to those described above, with or without allowing gaps. In calculating percent identity, typically exact matches are counted.

In another aspect, the present invention provides polynucleotides, oligonucleotides or nucleic acids encoding or relating to a polypeptide of the invention or a biologically active portion thereof, including, for example, nucleic acid molecules sufficient for use as hybridization probes, PCR primers or sequencing primers for identifying, analyzing, mutating or amplifying the nucleic acids of the invention.

In one embodiment, the nucleic acid encodes a polypeptide comprising a mutation in the protease of HIV associated with an hypersusceptibility to a protease inhibitor, e.g., saquinavir, ritonavir, indinavir, nelfinavir, amprenavir and lopinavir. In one embodiment, the invention provides a nucleic acid encoding a polypeptide derived from the HIV protease and comprising one or more mutations associated with hypersusceptibility to a protease inhibitor. Nucleic acids of the invention include nucleic acids, polynucleotides and oligonucleotides that are modified or derived from these nucleic acid sequences. In one embodiment, the nucleic acid comprises a nucleotide analog.

In one embodiment, the nucleic acid is naturally-occurring. In another embodiment, said nucleic acid is artificially designed.

The nucleic acid can be any length. The nucleic acid can be, for example, at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 125, 150, 175, 200, 250, 300, 350, 375, 400, 425, 450, 475 or 500 nucleotides in length. The nucleic acid can be, for example, less than 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 125, 150, 175, 200, 250, 300, 350, 375, 400, 425, 450, 475, 500, 525, 550, 575, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 10000 nucleotides in length. In a preferred embodiment, the nucleic acid has a length and a sequence suitable for detecting a mutation described herein, for example, as a probe or a primer.

In one embodiment, the nucleic acid encodes a polypeptide that comprises one or more mutations associated with hypersusceptibility to one or more protease inhibitors. Table 1 provides a list of mutations associated with hypersusceptibility to protease inhibitors.

In another embodiment, the invention provides an oligonucleotide encoding a polypeptide derived from the HIV protease and comprising at least one mutation at an amino acid position selected from a group consisting of: 16, 20, 33, 36, 37, 39, 45, 65, 69, 77, 89 and 93. In one embodiment, the amino acid at position 33 is not F.

In another preferred embodiment, said oligonucleotide comprising said mutation comprises 15, 30, 45, 60, 75, 90, 105, 120, 135, 150, 180, 210, 240, 255, 270 or 285 contiguous nucleic acids of SEQ ID NO: 2, within which sequence said mutation or mutations can be present.

In another embodiment, the oligonucleotide comprising said mutation or mutations is at least 60%, but less than 100%, identical to an oligonucleotide having the nucleic acid sequence of SEQ ID NO:2; the oligonucleotide has an nucleic acid sequence that is greater than 70% identical to the nucleic acid sequence of SEQ ID NO:2; the oligonucleotide has an nucleic acid sequence that is greater than 80% identical to the nucleic acid sequence of SEQ ID NO:2; or the oligonucleotide has an nucleic acid sequence that is greater than 90% identical to the nucleic acid sequence of SEQ ID NO:2, wherein the mutation is associated with hypersusceptibility to a protease inhibitor. The percent identity of two nucleic acid sequences can be determined as described above.

In addition to the nucleotide sequence of SEQ ID NO: 2, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. Natural allelic variations can typically result in 1-5% variance in the nucleotide sequence of a given gene. Any and all such nucleotide variations and resulting amino acid variations or polymorphisms that are the result of natural allelic variation and that do not alter the functional activity are intended to be within the scope of the invention.

In another embodiment, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full length polypeptide of the invention for example, a fragment that can be used as a probe or primer or a fragment encoding a biologically active portion of a polypeptide of the invention. The probe can comprise a labeled group attached thereto, e.g., a radioisotope, a fluorescent compound, an enzyme, or an enzyme co-factor. In various embodiments, the nucleic acid molecules of the invention can be modified at the base moiety, sugar moiety or phosphate backbone.

In another aspect, the invention provides a method for determining whether a HIV, e.g., HIV-1, has a decreased likelihood of being hypersusceptible to a protease inhibitor, comprising: detecting whether the protease encoded by said HIV-1 exhibits the presence or absence of a mutation negatively associated with hypersusceptibility to said protease inhibitor at amino acid position 10, 15, 36, 41, 57, 60, 63, 71 or 93 of an amino acid sequence of said protease, wherein the presence of said mutation indicates that the HIV has a decreased likelihood of being hypersusceptible to the protease inhibitor.

In another aspect, the invention provides a method for determining whether an individual infected with HIV, e.g., HIV-1, has a decreased likelihood of being hypersusceptible to treatment with a protease inhibitor, comprising detecting, in a sample from said individual, the presence or absence of a mutation negatively associated with hypersusceptibility to treatment with said protease inhibitor at amino acid position 10, 15, 36, 41, 57, 60, 63, 71 or 93 of the amino acid sequence of the protease of the HIV-1, wherein the presence of said mutation indicates that the individual has a decreased likelihood of being hypersusceptible to treatment with the protease inhibitor.

5.4 Finding Hypersusceptibility-Associated Viral Mutations

In another aspect, the present invention provides methods for finding susceptibility-associated mutation in a virus or a derivative of the virus.

5.4.1 The Virus and Viral Samples

A hypersusceptibility-associated mutation ("HSAM") according to the present invention can be present in any type of virus, for example, any virus found in animals. In one embodiment of the invention, the virus includes viruses known to infect mammals, including dogs, cats, horses, sheep, cows etc. In a preferred embodiment, the virus is known to infect primates. In an even more preferred embodiment the virus is known to infect humans. Examples of human viruses include, but are not limited to, human immunodeficiency virus ("HIV"), herpes simplex virus, cytomegalovirus virus, varicella zoster virus, other human herpes viruses, influenza A virus, respiratory syncytial virus, hepatitis A, B and C viruses, rhinovirus, and human papilloma virus. In a preferred embodiment of the invention, the virus is HIV. Preferably, the virus is human immunodeficiency virus type 1 ("HIV-1"). The foregoing are representative of certain viruses for which there is presently available anti-viral chemotherapy and represent the viral families retroviridae, herpesviridae, orthomyxoviridae, paramxyxovirus, picornavirus, flavivirus, pneumovirus and hepadnaviridae. This invention can be used with other viral infections due to other viruses within these families as well as viral infections arising from viruses in other viral families for which there is or there is not a currently available therapy.

A HSAM according to the present invention can be found in a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, a HSAM according to the present invention is present in a virus that can be obtained from a culture. In some embodiments, the culture can be obtained from a laboratory. In other embodiments, the culture can be obtained from a collection, for example, the American Type Culture Collection.

In certain embodiments, a HSAM according to the present invention is present in a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. Pat. Nos. 5,837,464 and 6,242,187 and PCT publication, WO 99/67427, each of which is incorporated herein by reference. In a preferred embodiment, the genes can be those that encode for a protease or reverse transcriptase.

In another embodiment, the intact virus need not be used. Instead, a part of the virus incorporated into a vector can be used. Preferably that part of the virus is used that is targeted by an anti-viral drug.

In another embodiment, a HSAM according to the present invention is present in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure. In one embodiment, the virus is HIV and the selective pressure is a protease inhibitor. In another embodiment, the virus is HIV-1 and the selective pressure is a protease inhibitor. Any protease inhibitor can be used to apply the selective pressure. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir. In another embodiment, the protease inhibitor is amprenavir. By treating HIV cultured in vitro with a protease inhibitor, e.g., amprenavir, one can select for mutant strains of HIV that have an increased resistance to said protease inhibitor, e.g., amprenavir. The stringency of the selective pressure can be manipulated to increase or decrease the survival of viruses not having the selected-for characteristic.

In another aspect, a HSAM according to the present invention is made by mutagenizing a virus, a viral genome, or a part of a viral genome. Any method of mutagenesis known in the art can be used for this purpose. In one embodiment, the mutagenesis is essentially random. In another embodiment, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, *Proc. Nat. Acad. Sci. USA* 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, a mutation that might affect the sensitivity of a virus to an anti-viral therapy is made using site-directed mutagenesis. Any method of site-directed mutagenesis known in the art can be used (see e.g., Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology,* Greene Publishing Associates and Wiley Interscience, NY). The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV protease. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains having decreased susceptibility to the anti-viral treatment. In another embodiment, the mutagenized nucleotides encode amino acid residues that are adjacent to or near in the primary sequence of the protein residues known or suspected to interact with an anti-viral compound or known or suspected to be mutated in viral strains having decreased susceptibility to an anti-viral treatment. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having decreased susceptibility to an anti-viral treatment. In another embodiment, the mutagenized nucleotides encode amino acid residues in or near the active site of a protein that is known or suspected to bind to an anti-viral compound. See, e.g., Sarkar and Sommer, 1990, *Biotechniques,* 8:404-407.

5.4.2 Dectecting the Presence or Absence of Mutations in a Virus

The presence or absence of a RAM according to the present invention in a virus can be detected by any means known in the art for detecting a mutation. The mutation can be detected in the viral gene that encodes a particular protein, or in the protein itself, i.e., in the amino acid sequence of the protein.

In one embodiment, the mutation is in the viral genome. Such a mutation can be in, for example, a gene encoding a viral protein, in a cis or trans acting regulatory sequence of a gene encoding a viral protein, an intergenic sequence, or an intron sequence. The mutation can affect any aspect of the structure, function, replication or environment of the virus that changes its susceptibility to an anti-viral treatment. In one embodiment, the mutation is in a gene encoding a viral protein that is the target of an anti-viral treatment.

A mutation within a viral gene can be detected by utilizing a number of techniques. Viral DNA or RNA can be used as the starting point for such assay techniques, and may be isolated according to standard procedures which are well known to those of skill in the art.

The detection of a mutation in specific nucleic acid sequences, such as in a particular region of a viral gene, can be accomplished by a variety of methods including, but not limited to, restriction-fragment-length-polymorphism detection based on allele-specific restriction-endonuclease cleavage (Kan and Dozy, 1978, *Lancet* ii:910-912), mismatch-repair detection (Faham and Cox, 1995, *Genome Res* 5:474-482), binding of MutS protein (Wagner et al., 1995, *Nucl Acids Res* 23:3944-3948), denaturing-gradient gel electrophoresis (Fisher et al., 1983, *Proc. Natl. Acad. Sci. U.S.A.* 80:1579-83), single-strand-conformation-polymorphism detection (Orita et al., 1983, *Genomics* 5:874-879), RNAase cleavage at mismatched base-pairs (Myers et al., 1985, *Science* 230:1242), chemical (Cotton et al., 1988, *Proc. Natl. Acad. Sci. U.S.A.* 85:4397-4401) or enzymatic (Youil et al., 1995, *Proc. Natl. Acad. Sci. U.S.A.* 92:87-91) cleavage of heteroduplex DNA, methods based on oligonucleotide-specific primer extension (Syvänen et al., 1990, *Genomics* 8:684-692), genetic bit analysis (Nikiforov et al., 1994, *Nucl Acids Res* 22:4167-4175), oligonucleotide-ligation assay (Landegren et al., 1988, *Science* 241:1077), oligonucleotide-specific ligation chain reaction ("LCR") (Barrany, 1991, *Proc. Natl.*

Acad. Sci. U.S.A. 88:189-193), gap-LCR (Abravaya et al., 1995, Nucl Acids Res 23:675-682), radioactive or fluorescent DNA sequencing using standard procedures well known in the art, and peptide nucleic acid (PNA) assays (Orum et al., 1993, Nucl. Acids Res. 21:5332-5356; Thiede et al., 1996, Nucl. Acids Res. 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, J. Mol. Biol. 98:503-517), single stranded conformational polymorphism analyses (SSCP) (Orita et al., 1989, Proc. Natl Acad. Sci. USA 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods for the detection of a gene-specific mutation can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine whether a gene mutation exists.

Additionally, the nucleic acid can be sequenced by any sequencing method known in the art. For example, the viral DNA can be sequenced by the dideoxy method of Sanger et al., 1977, Proc. Natl. Acad. Sci. USA 74:5463, as further described by Messing et al., 1981, Nuc. Acids Res. 9:309, or by the method of Maxam et al., 1980, Methods in Enzymology 65:499. See also the techniques described in Sambrook et al., 2001, Molecular Cloning: A Laboratory Manual, Cold Spring Harbor Laboratory, 3$^{rd}$ ed., NY; and Ausubel et al., 1989, Current Protocols in Molecular Biology, Greene Publishing Associates and Wiley Interscience, NY.

Antibodies directed against the viral gene products, i.e., viral proteins or viral peptide fragments can also be used to detect mutations in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

5.5 Measuring Phenotypic Hypersusceptibility of a Mutant Virus

Any method known in the art can be used to determine the phenotypic susceptibility of a mutant virus or population of viruses to an anti-viral therapy. See e.g., U.S. Pat. Nos. 5,837, 464 and 6,242,187, incorporated herein by reference in their entireties. In some embodiments a phenotypic analysis is performed, i.e., the susceptibility of the virus to a given anti-viral agent is assayed with respect to the susceptibility of a reference virus without the mutations. This is a direct, quantitative measure of drug susceptibility and can be performed by any method known in the art to determine the susceptibility of a virus to an anti-viral agent. An example of such methods includes, but is not limited to, determining the fold change in $IC_{50}$ values with respect to a reference virus. Phenotypic testing measures the ability of a specific viral strain to grow in vitro in the presence of a drug inhibitor. A virus is more susceptible to a particular drug when less of the drug is required to inhibit viral activity, versus the amount of drug required to inhibit the reference virus.

In one embodiment, a phenotypic analysis is performed and used to calculate the $IC_{50}$ or $IC_{90}$ of a drug for a viral strain. The results of the analysis can also be presented as fold-change in $IC_{50}$ or $IC_{90}$ for each viral strain as compared with a drug-susceptible control strain or a prior viral strain from the same patient. Because the virus is directly exposed to each of the available anti-viral medications, results can be directly linked to treatment response. For example, if the patient virus shows resistance to a particular drug, that drug is avoided or omitted from the patient's treatment regimen, allowing the physician to design a treatment plan that is more likely to be effective for a longer period of time. Conversely, if the patient virus shows increased susceptibility to a particular drug, that drug can be repeated.

In another embodiment, the phenotypic analysis is performed using recombinant virus assays ("RVAs"). RVAs use virus stocks generated by homologous recombination between viral vectors and viral gene sequences, amplified from the patient virus. In some embodiments, the viral vector is a HIV vector and the viral gene sequences are protease and/or reverse transcriptase sequences.

In a preferred embodiment, the phenotypic analysis is performed using PHENOSENSE™ (ViroLogic Inc., South San Francisco, Calif.). See Petropoulos et al., 2000, Antimicrob. Agents Chemother. 44:920-928; U.S. Pat. Nos. 5,837,464 and 6,242,187. PHENOSENSE™ is a phenotypic assay that achieves the benefits of phenotypic testing and overcomes the drawbacks of previous assays. Because the assay has been automated, PHENOSENSE™ offers higher throughput under controlled conditions. The result is an assay that accurately defines the susceptibility profile of a patient's HIV isolates to all currently available antiretroviral drugs, and delivers results directly to the physician within about 10 to about 15 days of sample receipt. PHENOSENSE™ is accurate and can obtain results with only one round of viral replication, thereby avoiding selection of subpopulations of virus. The results are quantitative, measuring varying degrees of drug susceptibility, and sensitive—the test can be performed on blood specimens with a viral load of about 500 copies/mL and can detect minority populations of some drug-resistant virus at concentrations of 10% or less of total viral population. Furthermore, the results are reproducible and can vary by less than about 1.4-2.5 fold, depending on the drug, in about 95% of the assays performed.

PHENOSENSE™ can be used with nucleic acids from amplified viral gene sequences. As discussed in Section 5.4.1, the sample containing the virus may be a sample from a human or an animal infected with the virus or a sample from a culture of viral cells. In one embodiment, the viral sample comprises a genetically modified laboratory strain.

A resistance test vector ("RTV") can then be constructed by incorporating the amplified viral gene sequences into a replication defective viral vector by using any method known in the art of incorporating gene sequences into a vector. In one embodiment, restrictions enzymes and conventional cloning methods are used. See Sambrook et al., 2001, *Molecular Cloning: A Laboratory Manual,* Cold Spring Harbor Laboratory, 3$^{rd}$ ed., NY; and Ausubel et al., 1989, *Current Protocols in Molecular Biology,* Greene Publishing Associates and Wiley Interscience, NY. In a preferred embodiment, ApaI and PinAI restriction enzymes are used. Preferably, the replication defective viral vector is the indicator gene viral vector ("IGVV"). In a preferred embodiment, the viral vector contains a means for detecting replication of the RTV. Preferably, the viral vector contains a luciferase expression cassette.

The assay can be performed by first co-transfecting host cells with RTV DNA and a plasmid that expresses the envelope proteins of another retrovirus, for example, amphotropic murine leukemia virus (MLV). Following transfection, virus particles can be harvested and used to infect fresh target cells. The completion of a single round of viral replication can be detected by the means for detecting replication contained in the vector. In a preferred embodiment, the completion of a single round of viral replication results in the production of luciferase. Serial concentrations of anti-viral agents can be added at either the transfection step or the infection step.

Susceptibility to the anti-viral agent can be measured by comparing the replication of the vector in the presence and absence of the anti-viral agent. For example, susceptibility to the anti-viral agent can be measured by comparing the luciferase activity in the presence and absence of the anti-viral agent. Susceptible viruses would produce low levels of luciferase activity in the presence of anti-viral agents, whereas viruses with reduced susceptibility would produce higher levels of luciferase activity.

In preferred embodiments, PHENOSENSE™ is used in evaluating the phenotypic susceptibility of HIV-1 to anti-viral drugs. Preferably, the anti-viral drug is a protease inhibitor. Examples of protease inhibitors include, but are not limited to, saquinavir, ritonavir, indinavir, nelfinavir, amprenavir and lopinavir. In preferred embodiments, the reference viral strain is HIV strain NL4-3 or HXB-2.

In one embodiment, viral nucleic acid, for example, HIV-1 RNA is extracted from plasma samples, and a fragment of, or entire viral genes could be amplified by methods such as, but not limited to PCR. See, e.g., Hertogs et al., 1998, *Antimicrob Agents Chemother* 42(2):269-76. In one example, a 2.2-kb fragment containing the entire HIV-1 PR- and RT-coding sequence is amplified by nested reverse transcription-PCR. The pool of amplified nucleic acid, for example, the PR-RT-coding sequences, is then co-transfected into a host cell such as CD4+ T lymphocytes (MT4) with the pGEMT3deltaPRT plasmid from which most of the PR (codons 10 to 99) and RT (codons 1 to 482) sequences are deleted. Homologous recombination leads to the generation of chimeric viruses containing viral coding sequences, such as the PR- and RT-coding sequences derived from HIV-1 RNA in plasma. The susceptibilities of the chimeric viruses to all currently available anti-viral agents targeting the products of the transfected genes (proRT and/or PR inhibitors, for example), can be determined by any cell viability assay known in the art. For example, an MT4 cell-3-(4,5-dimethylthiazol-2-yl)-2,5-diphenyltetrazolium bromide-based cell viability assay can be used in an automated system that allows high sample throughput. The profile of resistance to all the anti-viral agents, such as the RT and PR inhibitors can be displayed graphically in a single PR-RT-Antivirogram.

Other assays for evaluating the phenotypic susceptibility of a virus to anti-viral drugs known to one of skill in the art can be used. See, e.g., Shi and Mellors, 1997, *Antimicrob Agents Chemother.* 41(12):2781-85; Gervaix et al., 1997, *Proc Natl Acad Sci U.S.A.* 94(9):4653-8; Race et al., 1999, *AIDS* 13:2061-2068, incorporated herein by reference in their entireties.

In another embodiment, the susceptibility of a virus to treatment with an anti-viral treatment is determined by assaying the activity of the target of the anti-viral treatment in the presence of the anti-viral treatment. In one embodiment, the virus is HIV, the anti-viral treatment is a protease inhibitor, and the target of the anti-viral treatment is the HIV protease. See, e.g., U.S. Pat. Nos. 5,436,131, 6,103,462, incorporated herein by reference in their entireties.

5.6 Correlating Phenotypic and Genotypic Hypersusceptibility

Any method known in the art can be used to determine whether a mutation is correlated with an increase in susceptibility of a virus to an anti-viral treatment and thus is a HSAM according to the present invention. In one embodiment, P values are used to determine the statistical significance of the correlation, such that the smaller the P value, the more significant the measurement. Preferably the P values will be less than 0.05. More preferably, P values will be less than 0.01. P values can be calculated by any means known to one of skill in the art. In one embodiment, P values are calculated using Fisher's Exact Test. See, e.g., David Freedman, Robert Pisani & Roger Purves, 1980, STATISTICS, W. W. Norton, New York. In another embodiment, P values are calculated using the t-test and the non-parametric Kruskal-Wallis test (Statview 5.0 software, SAS, Cary, N.C.).

In a preferred embodiment, numbers of samples with the mutation being analyzed that have an $IC_{50}$ fold change equal to or less than the $10^{th}$ percentile for each protease inhibitors' fold change distribution are compared to numbers of samples without the mutation. A 2×2 table can be constructed and the P value can be calculated using Fisher's Exact Test (see Example 1). P values smaller than 0.05 or 0.01 can be classified as statistically significant.

5.7 Determining Hypersusceptibility to the Anti-Viral Treatment

In another aspect, the present invention provides a method for determining a virus' hypersusceptibility to anti-viral treatment. Hypersusceptibility-associated mutations (HSAMs) can be identified and correlated with increased susceptibility of a virus to an anti-viral treatment as described in Sections 5.3-5.6 above. The presence of a HSAM in a virus can be detected by any means known in the art, e.g., as discussed in Section 5.4.2 above. The presence of a HSAM in the virus can indicate that the virus has an increased likelihood of having increased susceptibility for the anti-viral treatment. In one embodiment, the virus is human immunodeficiency virus (HIV). In another embodiment, the virus is human immunodeficiency virus type-1 (HIV-1). In another embodiment, the anti-viral treatment is a protease inhibitor. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir.

In another embodiment, the invention provides a method for determining whether a HIV has an increased likelihood of being hypersusceptible to treatment with a protease inhibitor, comprising: detecting whether the protease encoded by said HIV exhibits the presence or absence of a mutation associated with hypersusceptibility to treatment with said protease inhibitor at amino acid position 16, 20, 33, 36, 37, 39, 45, 65, 69, 77, 89 or 93 of an amino acid sequence of said protease, wherein the presence of said mutation indicates that the HIV has an increased likelihood of being hypersusceptible to treatment with the protease inhibitor, with the proviso that said mutation is not L33F.

In another aspect, the present invention provides a method for determining the susceptibility of an individual infected with a virus to anti-viral treatment. Hypersusceptibility-associated mutations (HSAMs) can be identified and correlated with increased susceptibility of a virus to an anti-viral treatment as described in Sections 5.3-5.6 above. The presence of a HSAM in a virus present in a sample from the individual can be detected by any means known in the art, e.g., as discussed in Section 5.4.2 above. The presence of a HSAM in the virus can indicate that the individual has an increased likelihood of having increased susceptibility for the anti-viral treatment. In one embodiment, the virus is HIV. In another embodiment, the virus is HIV-1. In another embodiment, the anti-viral treatment is a protease inhibitor. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir.

In another embodiment, the invention provides a method for determining whether an individual infected with HIV has an increased likelihood of being hypersusceptible to treatment with a protease inhibitor, comprising detecting, in a sample from said individual, the presence or absence of a mutation associated with hypersusceptibility to treatment with said protease inhibitor at amino acid position 16, 20, 33, 36, 37, 39, 45, 65, 69, 77, 89 or 93 of the amino acid sequence of the protease of the HIV, wherein the presence of said mutation indicates that the individual has an increased likelihood of being hypersusceptible to treatment with the protease inhibitor, with the proviso that said mutation is not L33F.

5.8 Constructing an Algorithm

In one aspect, the present invention provides a method of constructing an algorithm that correlates genotypic data about a virus with phenotypic data about the virus. In one embodiment, the phenotypic data relate to the susceptibility of the virus to an anti-viral treatment. In another embodiment, the anti-viral treatment is an anti-viral compound. In another embodiment, the anti-viral compound is a protease inhibitor. Examples of protease inhibitors include, but are not limited to, saquinavir, ritonavir, indinavir, nelfinavir, amprenavir and lopinavir.

In one embodiment, the method of constructing the algorithm comprises creating a rule or rules that correlate genotypic data about a set of viruses with phenotypic data about the set of viruses.

In one embodiment, a data set comprising genotypic and phenotypic data about each virus in a set of viruses is assembled. Any method known in the art can be used to collect genotypic data about a virus. Examples of methods of collecting such data are provided above. Any method known in the art can be used for collecting phenotypic data about a virus. Examples of such methods are provided above. In a preferred embodiment, the data set comprises one or more HSAMs as described above. In one embodiment, each genotypic datum is the sequence of all or part of a viral protein of a virus in the set of viruses. In another embodiment, each genotypic datum in the data set is a single amino acid change in a protein encoded by the virus, relative to a reference protein in the reference virus. In other embodiments, the genotype comprises two, three, four, five, six, seven, eight, nine, ten or more amino acid changes in the viral protein. In another embodiment, the virus is HIV, and the protein is HIV protease. In a preferred embodiment, the virus is HIV-1. In another embodiment, the reference protein is the protease from NL4-3 HIV.

In one embodiment, each phenotypic datum in the data set is the susceptibility to an anti-viral treatment of a virus in the set of viruses. In one embodiment, the anti-viral treatment is an anti-viral compound. In another embodiment, the anti-viral compound is a protease inhibitor. In one embodiment, the susceptibility is measured as a change in the susceptibility of the virus relative to a reference virus. In another embodiment, the susceptibility is measured as a change in the $IC_{50}$ of the virus relative to a reference virus. In another embodiment, the change in $IC_{50}$ is represented as the fold-change in $IC_{50}$. In one embodiment the virus is HIV. In a preferred embodiment, the virus is HIV-1. In another preferred embodiment, the reference HIV is NL4-3 HIV.

The genotypic and phenotypic data in the data set can be represented or organized in any way known in the art. In one embodiment, the data are displayed in the form of a graph. In this type of representation, the y-axis represents the fold change in $IC_{50}$ of a virus in the data set relative to a reference virus. Each point on the graph corresponds to one virus in the data set. The x-axis represents the number of mutations that a virus in the data set has. The position of the point indicates both the number of mutations and the fold change in anti-viral therapy treatment that the virus has, both measured relative to a reference strain. In another embodiment, the genotypic and phenotypic data in the data set are displayed in the form of a chart.

In one aspect, an algorithm is formulated that correlates the genotypic data with the phenotypic data in the data set. In one embodiment, a phenotypic cutoff point is defined. In a preferred embodiment, the phenotype is susceptibility to an anti-viral treatment. In another embodiment, the phenotype is change in sensitivity to an anti-viral treatment relative to a reference virus. In another embodiment, the cutoff point is the value below which a virus or population of viruses is defined as phenotypically hypersusceptible to the anti-viral therapy and above which a virus or population of viruses is, although phenotypically sensitive, not hypersusceptible to the anti-viral therapy. In other embodiments, the cutoff point is a fold change of 0.9, 0.8, 0.7, 0.6, 0.5, 0.4, 0.3, 0.2, 0.1, 0.07, 0.05, 0.03, 0.02 or 0.01 with reference to the $IC_{50}$ of a reference virus. In a preferred embodiment, the virus is HIV and the anti-viral therapy is treatment with a protease inhibitor. In a more preferred embodiment, the virus is HUV-1.

In another embodiment, the phenotypic cutoff point is used to define a genotypic cutoff point. In one embodiment this is done by correlating the number of mutations in a virus of the data set with the phenotypic susceptibility of the virus. This can be done as discussed above. A genotypic cutoff point is selected such that most viruses having more than that number of mutations in the data set are phenotypically hypersusceptible ("PT-HS"), and most viruses having fewer than that number of mutations are not PT-HS. By definition, a virus in the data set with number of mutations equal to, or more than the genotypic cutoff is genotypically hypersusceptible ("GT-HS") to the anti-viral treatment, and a virus in the data set with fewer than the genotypic cutoff number of mutations is not GT-HS to the anti-viral treatment.

While this algorithm can provide a useful approximation of the relationship between the genotypic and phenotypic data in the data set, in most cases there will be a significant number of strains that are GT-HS, but not PT-HS, or PT-HS, but not GT-HS. Thus, in a preferred embodiment, the algorithm is further modified to reduce the percentage of discordant results in the data set. This is done, for example, by removing from the data set each data point that corresponds to a virus population comprising a mixture of mutations including the wild-type, at a single position considered by the algorithm tested.

In another embodiment, differential weight values are assigned to one or more mutations observed in the data set. An algorithm that does not include this step assumes that each mutation in the data set contributes equally to the overall resistance of a virus or population of viruses to an anti-viral therapy. In one embodiment, some mutations are "weighted," i.e., assigned an increased mutation score. A mutation can be assigned a weight of, for example, two, three, four, five, six, seven, eight or more. For example, a mutation assigned a weight of 2 will be counted as two mutations in a virus. Fractional weighting values can also be assigned. In another embodiment, values of less than 1, and of less than zero, can be assigned, wherein a mutation is associated with an decreased sensitivity of the virus to the anti-viral treatment.

One of skill in the art will appreciate that there is a tradeoff involved in assigning an increased weight to certain mutations. As the weight of the mutation is increased, the number of GT-HS, but not PT-HS discordant results may increase. Thus, assigning a weight to a mutation that is too great may increase the overall discordance of the algorithm. Accordingly, in one embodiment, a weight is assigned to a mutation that balances the reduction in PT-HS, but not GT-HS discordant results with the increase in GT-HS, but not PT-HS discordant results.

In another embodiment, the interaction of different mutations in the data set with each other is also factored into the algorithm. For example, it might be found that two or more mutations behave synergistically, i.e., that the coincidence of the mutations in a virus contributes more significantly to the hypersusceptibility of the virus than would be predicted based on the effect of each mutation independent of the other. Alternatively, it might be found that the coincidence of two or more mutations in a virus contributes less significantly to the hypersusceptibility of the virus than would be expected from the contributions made to resistance by each mutation when it occurs independently. Also, two or more mutations may be found to occur more frequently together than as independent mutations. Thus, in one embodiment, mutations occurring together are weighted together. For example, only one of the mutations is assigned a weight of 1 or greater, and the other mutation or mutations are assigned a weight of zero, in order to avoid an increase in the number of GT-HS, but not PT-HS discordant results.

In another aspect, the phenotypic cutoff point can be used to define a genotypic cutoff point by correlating the number as well as the class of mutations in a virus of the data set with the phenotypic hypersusceptibility of the virus. Examples of classes of mutations include, but are not limited to, primary amino acid mutations, secondary amino acid mutations, mutations in which the net charge on the polypeptide is conserved and mutations that do not alter the polarity, hydrophobicity or hydrophilicity of the amino acid at a particular position. Other classes of mutations that are within the scope of the invention would be evident to one of skill in the art, based on the teachings herein.

In one embodiment, an algorithm is constructed that factors in the requirement for one or more classes of mutations. In another embodiment, the algorithm factors in the requirement for a minimum number of one or more classes of mutations. In another embodiment, the algorithm factors in the requirement for a minimum number of primary or secondary mutations. In another embodiment, the requirement of a primary or a secondary mutation in combination with other mutations is also factored into the algorithm. For example, it might be found that a virus with a particular combination of mutations is hypersusceptible to an anti-viral treatment, whereas a virus with any mutation in that combination, alone or with other mutations that are not part of the combination, is not hypersusceptible to the anti-viral treatment.

By using, for example, the methods discussed above, the algorithm can be designed to achieve any desired result. In one embodiment, the algorithm is designed to maximize the overall concordance (the sum of the percentages of the PT-HS, GT-HS and the not PT-HS, not GT-HS groups, or 100 minus (percentage of the PT-HS, not GT-HS+ not PT-HS, GT-HS groups). In preferred embodiments, the overall concordance is greater than about 75%, 80%, 85%, 90% or 95%. In another embodiment, the algorithm is designed to minimize the percentage of PT-HS, not GT-HS results. In another embodiment, the algorithm is designed to minimize the percentage of not PT-HS, GT-HS results. In another embodiment, the algorithm is designed to maximize the percentage of not PT-HS, not GT-HS results. In another embodiment, the algorithm is designed to maximize the percentage of PT-HS, GT-HS results.

At any point during the construction of the algorithm, or after it is constructed, it can be further tested on a second data set. In one embodiment, the second data set consists of viruses that are not included in the data set, i.e., the second data set is a naive data set. In another embodiment, the second data set contains one or more viruses that were in the data set and one or more viruses that were not in the data set. Use of the algorithm on a second data set, particularly a naive data set, allows the predictive capability of the algorithm to be assessed. Thus, in one embodiment, the accuracy of an algorithm is assessed using a second data set, and the rules of the algorithm are modified as described above to improve its accuracy. In a preferred embodiment, an iterative approach is used to create the algorithm, whereby an algorithm is tested and then modified repeatedly until a desired level of accuracy is achieved.

5.9 Using an Algorithm to Predict the Hypersusceptibility of a Virus

In another aspect, the present invention also provides a method for using an algorithm of the invention to predict the phenotypic hypersusceptibility of a virus or a derivative of a virus to an anti-viral treatment based on the genotype of the virus. In one embodiment, the method comprises detecting, in the virus or derivative of the virus, the presence or absence of one or more HSAMs, applying the rules of the algorithm to the virus, wherein a virus that satisfies the rules of the algorithm is genotypically hypersusceptible to the anti-viral treatment, and a virus that does not satisfy the rules of the algorithm is not genotypically hypersusceptible to the anti-viral treatment. In another embodiment, the method comprises detecting, in the virus or derivative of the virus, the presence or absence of one or more HSAMs, applying the rules of the algorithm to the detected HSAMs, wherein a score equal to, or greater than the genotypic cutoff score indicates that the virus is genotypically hypersusceptible to the anti-viral treatment, and a score less than the genotypic cutoff score indicates that the virus is not genotypically hypersusceptible to the anti-viral treatment.

The algorithm of this invention can be used for any viral disease where anti-viral drug susceptibility is a concern, as discussed above in Section 5.4.1. In certain embodiments the assay of the invention can be used to determine the susceptibility of a retrovirus to an anti-viral drug. In a preferred embodiment, the retrovirus is HIV. Preferably, the virus is HIV-1.

The anti-viral agent of the invention could be any treatment effective against a virus. It is useful to the practice of this invention, for example, to understand the structure, life cycle and genetic elements of the viruses which can be tested in the drug susceptibility test of this invention. These would be known to one of ordinary skill in the art and provide, for example, key enzymes and other molecules at which the anti-viral agent can be targeted. Examples of anti-viral agents of the invention include, but are not limited to, nucleoside reverse transcriptase inhibitors such as AZT, ddl, ddC, d4T, 3TC, abacavir, nucleotide reverse transcriptase inhibitors such as tenofovir, non-nucleoside reverse transcriptase inhibitors such as nevirapine, efavirenz, delavirdine, fusion inhibitors such as T-20 and T-1249 and protease inhibitors such as saquinavir, ritonavir, indinavir, nelfinavir, amprenavir and lopinavir.

In some embodiments of the invention, the anti-viral agents are directed at retroviruses. In preferred embodiments, the anti-viral agents are protease inhibitors such as saquinavir, ritonavir, indinavir, nelfinavir, amprenavir and lopinavir.

Some mutations associated with hypersusceptibility to treatment with an anti-viral agent are known in the art, e.g., N88S for the protease inhibitor amprenavir. Ziermann et al., 2000, *J Virol* 74:4414-4419. Others can be determined by methods described in Sections 5.4-5.8 above. For example, Table 1 provides a list of mutations associated with hypersusceptibility to protease inhibitors.

5.10 Using an Algorithm to Predict the Effectiveness of Anti-Viral Treatment for an Individual In another aspect, the present invention also provides a method for using an algorithm of the invention to predict the effectiveness of an anti-viral treatment for an individual infected with a virus based on the genotype of the virus to the anti-viral treatment. In one embodiment, the method comprises detecting, in the virus or derivative of the virus, the presence or absence of one or more HSAMs, applying the rules of the algorithm to the virus, wherein a virus that satisfies the rules of the algorithm is genotypically hypersusceptible to the anti-viral treatment, and a virus that does not satisfy the rules of the algorithm is not genotypically hypersusceptible to the anti-viral treatment. In another embodiment, the method comprises detecting, in the virus or a derivative of the virus, the presence or absence of one or more HSAMs, applying the rules of the algorithm to the detected HSAMs, wherein a score equal to, or greater than the genotypic cutoff score indicates that the virus is genotypically hypersusceptible to the anti-viral treatment, and a score less than the genotypic cutoff score indicates that the virus is not genotypically hypersusceptible to the anti-viral treatment.

As described in Section 5.4.1 above, the algorithm of the invention can be used for any viral disease where anti-viral drug susceptibility is a concern and the anti-viral agent of the invention could be any treatment effective against a virus. In certain embodiments the assay of the invention is used to determine the susceptibility of a retrovirus to an anti-viral drug. In a preferred embodiment, the retrovirus is HIV. Preferably, the virus is HIV-1. In some embodiments of the invention, the anti-viral agents are directed at retroviruses. In preferred embodiments, the anti-viral agents are protease inhibitors such as saquinavir, ritonavir, indinavir, nelfinavir, amprenavir and lopinavir.

As described in Section 5.9 above, mutations associated with hypersusceptibility to treatment with an anti-viral agent may be obtained from the art or determined by methods described above in Sections 5.4-5.8.

In some embodiments, the present invention provides a method for monitoring the effectiveness of an anti-viral treatment in an individual infected with a virus and undergoing or having undergone prior treatment with the same or different anti-viral treatment, comprising, detecting, in a sample of said individual, the presence or absence of an amino acid residue associated with hypersusceptibility to treatment the anti-viral treatment, wherein the presence of the residue correlates with an hypersusceptibility to treatment with the anti-viral treatment. In a preferred embodiment, the anti-viral treatment is a protease inhibitor.

5.11 Correlating Hypersusceptibility to One Anti-Viral Treatment with Hypersusceptibility to Another Anti-Viral Treatment In another aspect, the present invention provides a method for using an algorithm of the invention to predict the effectiveness of an anti-viral treatment against a virus based on the genotypic susceptibility of the virus to a different anti-viral treatment. In one embodiment, the method comprises detecting, in a virus or a derivative of a virus, the presence or absence of one or more mutations correlated with hypersusceptibility to an anti-viral treatment and applying the rules of an algorithm of the invention to the detected mutations, wherein a score equal to, or greater than the genotypic cutoff score indicates that the virus is genotypically hypersusceptible to a different anti-viral treatment, and a score less than the genotypic cutoff score indicates that the virus is not genotypically hypersusceptible to a different anti-viral treatment. In another embodiment, the two anti-viral treatments affect the same viral protein. In another embodiment, the two anti-viral treatments are both protease inhibitors. Examples of protease inhibitors include, but are not limited to, saquinavir, ritonavir, indinavir, nelfinavir, amprenavir and lopinavir. In another embodiment, a mutation correlated with resistance to one protease inhibitor is also correlated with resistance to another protease inhibitor.

6. EXAMPLES

The following examples are provided to illustrate certain aspects of the present invention and not intended as limiting the subject matter thereof.

6.1 Example 1

Analysis of Patient Samples to Identify Hypersusceptibility-Associated Mutations This example demonstrates a method of analyzing patient samples so as to identify mutations that are associated with hypersusceptibility to protease inhibitors.

In order to determine the relationship between an HIV-1 strain's protease sequence and its susceptibility to treatment with a protease inhibitor, a data set of patient plasma samples was analyzed genotypically as well as phenotypically. The phenotypic assay was conducted using the PHENOSENSE™ (Virologic, South San Francisco, Calif.) HIV assay (Petropoulos et al., 2000, *Antimicrob. Agents Chemother.* 44:920-928; U.S. Pat. Nos. 5,837,464 and 6,242,187). Plasma samples were collected from HIV-1-infected patients. Repeat samples from the same patient were removed to prevent possible bias resulting from unique combinations of mutations. In addition, samples with any resistance-selected mutation (see Table 2) in HIV-I protease or HIV-1 reverse transcriptase were excluded. This resulted in a data set of 1515 samples. Positions in the protease that varied in at least 1% of the sample set (i.e., at least 15 samples) were considered in the analysis. $IC_{50}$ values for several protease inhibitors were obtained for the HIV-1 from the patient samples. This was compared to the $IC_{50}$ for the protease inhibitors against the NMA-3 (GenBank Accession No. AF324493) reference viral strain. Phenotypic data were expressed as "fold change" (or log fold change) in 50% inhibitory concentration ($IC_{50}$) of the protease inhibitor. The fold $IC_{50}$ values were calculated by dividing the $IC_{50}$ of the protease inhibitor against the HIV-1 from the patient plasma sample by the $IC_{50}$ for the protease inhibitor against the NL4-3 (GenBank Accession No. AF324493) reference viral strain.

Figure 2:
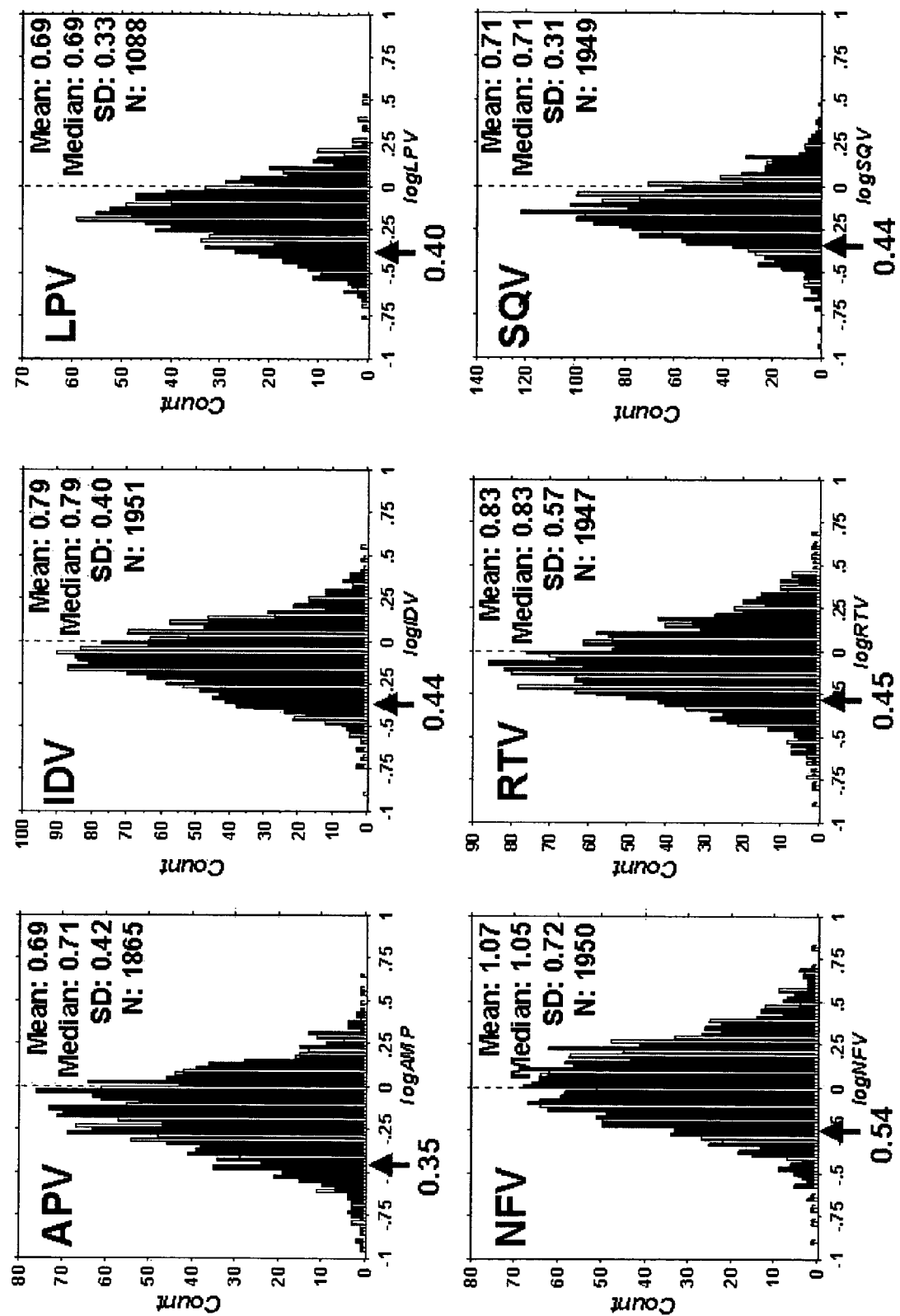
FIG. 2 shows the protease inhibitor fold change distributions.

As seen in FIG. 2, the fold change values observed were normally distributed for all the protease inhibitors. Table 3 shows the mean, median, $90^{th}$ and $10^{th}$ percentile values for the fold change (FC) for amprenavir ("APV"), indinavir ("IDV"), nelfinavir ("NFV"), ritonavir ("RTV"), saquinavir ("SQV") and lopinavir ("LPV").

Figure 3:
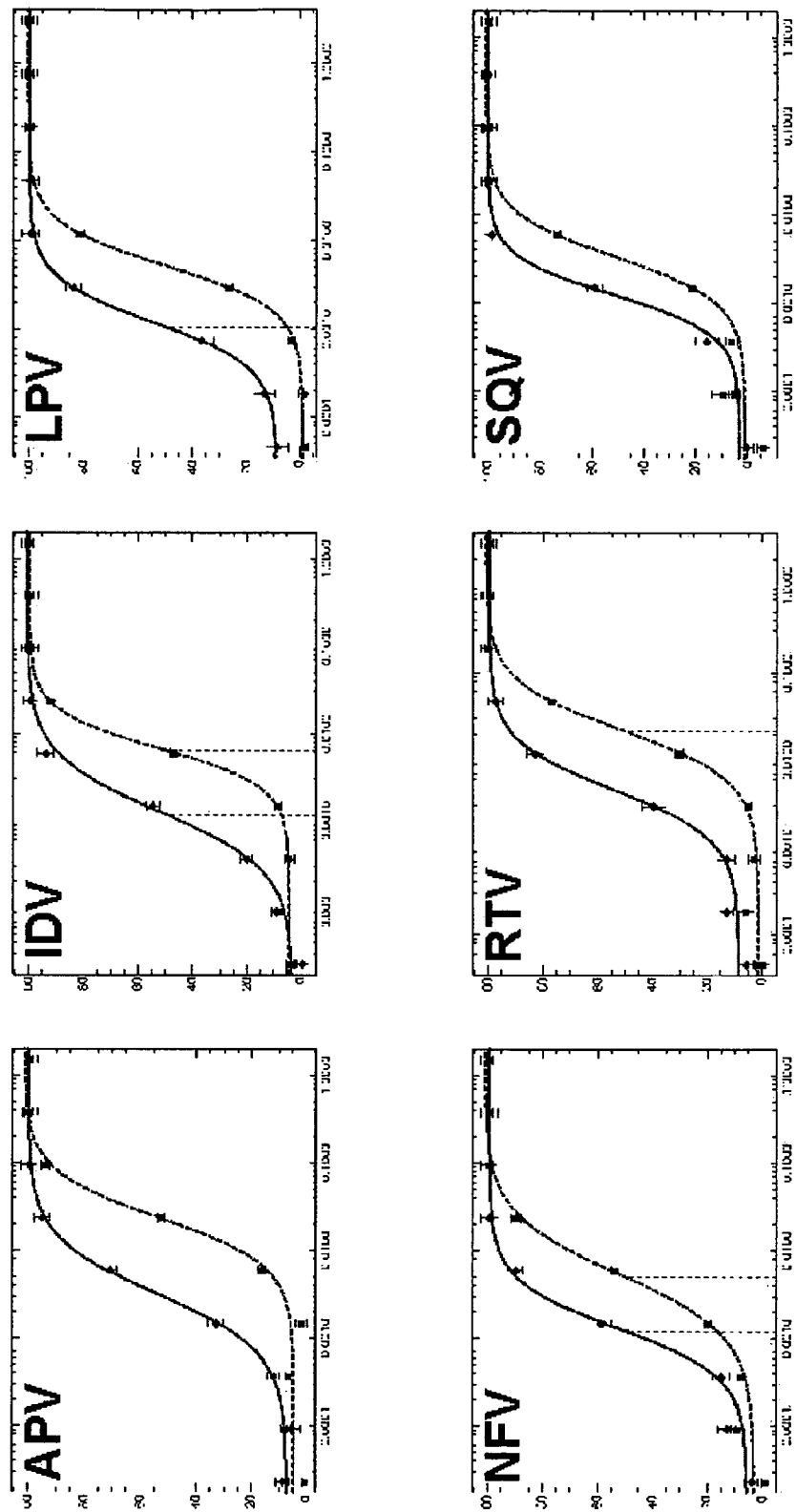
FIG. 3 shows inhibition curves for a sample with hypersusceptibility to protease inhibitors.

Hypersusceptibility was defined as a fold change equal to or less than the $10^{th}$ percentile for each protease inhibitors' fold change distribution. FIG. 3 shows inhibition curves for different protease inhibitors for the wild type or reference virus as well as for a sample with hypersusceptibility to the different protease inhibitors. Percent inhibition is plotted on the Y-axis and protease inhibitor concentration (in mM) is plotted on the X-axis. As can be seen in the figure, the curve for the sample with hypersusceptibility to the protease inhibitors (solid curve) is shifted to the left as compared to the curve for the wild type virus, indicating a lower $IC_{50}$ (and thus an increased susceptibility) for the sample as compared to the wild-type.

Figure 4:
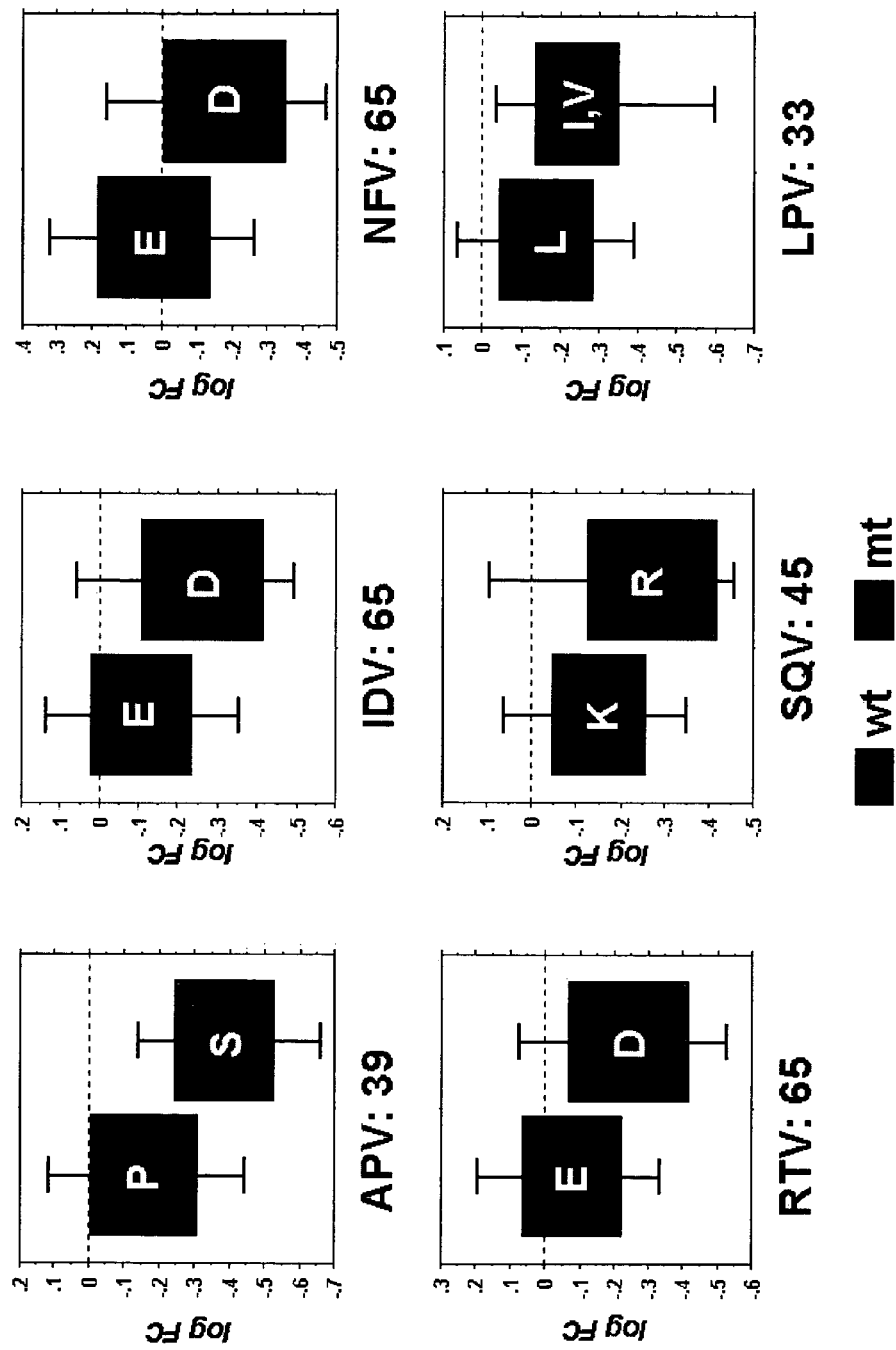
FIG. 4 shows protease inhibitor susceptibility for samples with mutations associated with hypersusceptibility to protease inhibitors.

Mean log-transformed fold-changes of samples with or without mutations at each position were compared by the t-test for comparison of means and the non-parametric Kruskal-Wallis test. The numbers of samples defined as hypersusceptible with or without mutations at each position were compared using Fisher's Exact test. P-values of 0.05 or less were considered significant. Table 1 lists the positions that were found to be associated with hypersusceptibility for the different protease inhibitors by all three statistical tests. The mutations in the column "Positive Association" were over-represented in the samples found to be hypersusceptible to the protease inhibitor and those mutations in the "Negative Association" column were under-represented in the samples found to be hypersusceptible to the protease inhibitor. A virus with mutations at positions listed in the "Negative Association" column is less likely to have hypersusceptibility to protease inhibitors. The underlined positions were associated with the largest changes in mean fold change. FIG. 4 shows the log FC for the wild type virus ("wt"), a mixture of samples containing the wild type virus and the indicated mutant ("mix") and a sample containing the indicated mutant ("mt") for the different protease inhibitors. Those mutants were selected that had the largest changes in mean fold change (e.g., P39 for APV, E65 for IDV and so on).

Figure 5:
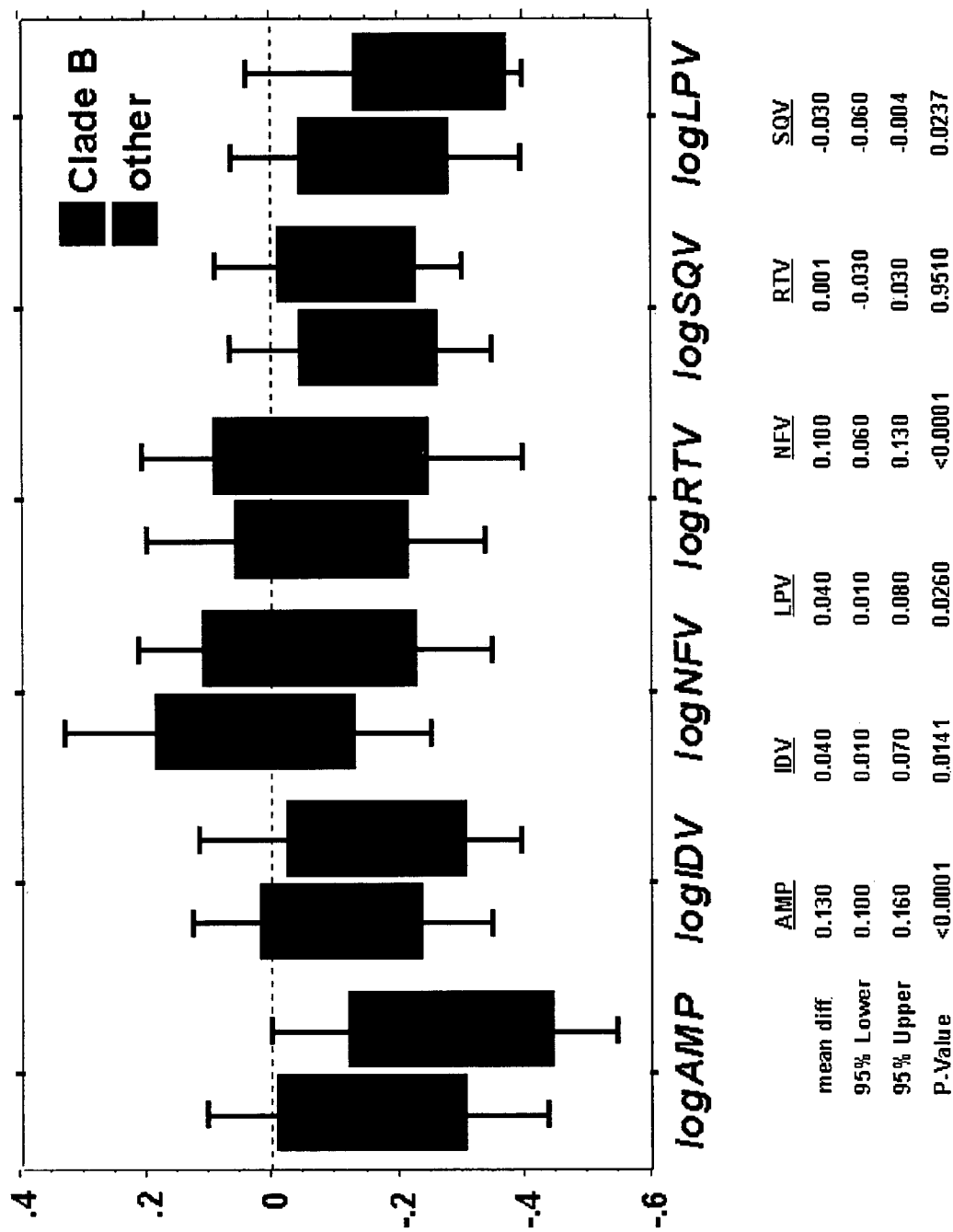
FIG. 5 shows protease inhibitor susceptibility for B clade and non-B clade viruses.

Some of the mutations listed in Table 1 and associated with hypersusceptibility often occurred together, such as mutations at positions 69+89, 20+36, and 36+89. Since M361, R41K, H69K, and L89M are signature mutations for non-B clade HIV, it is possible that non-B clade HIV may have increased susceptibility to some protease inhibitors. FIG. 5 shows the protease inhibitor susceptibility for B clade and non-B clade viruses. As can be seen in the figure, the non-B clade viruses typically (with the exception of SQV) have higher susceptibility to protease inhibitors than do B clade viruses. This has important implications in the treatment of an individual infected with HIV-1. There is an increased likelihood that an individual infected with a non-B clade HIV will be hypersusceptible to a protease inhibitor as compared to an individual infected with a B clade HIV.

Figure 6:
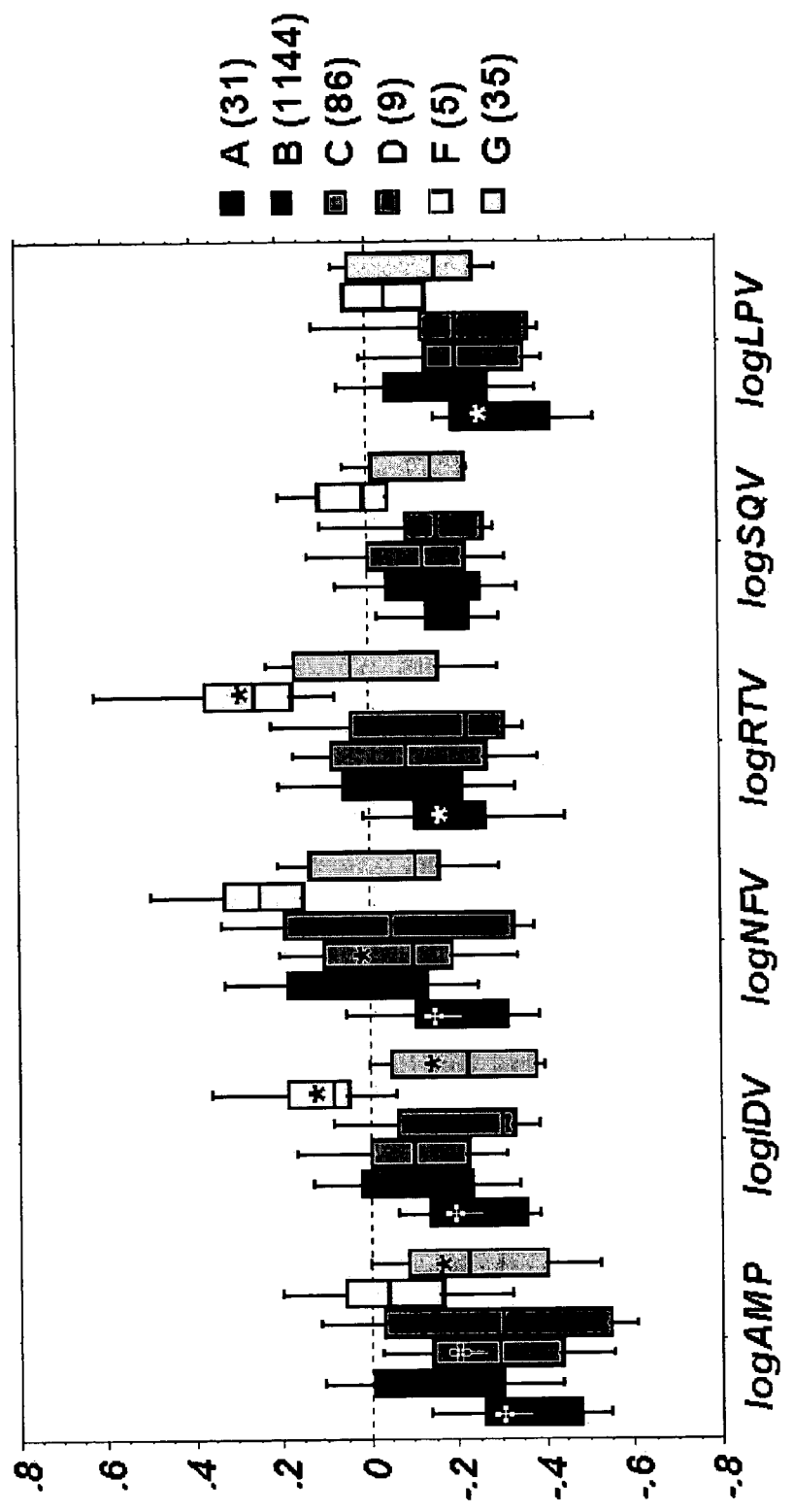
FIG. 6 shows protease inhibitor susceptibility for the different clade viruses.

FIG. 6 shows the protease inhibitor susceptibility for HIV split by clade. The clade HIV and the number of samples containing each clade are indicated to the right of the figure. As can be seen in the figure, different clade HIV have different susceptibilities to the different protease inhibitors. If the clade HIV infecting an individual is known, then the protease inhibitor to which that clade HIV is most susceptibility can be used.

6.2 Example 2

Figure 7:
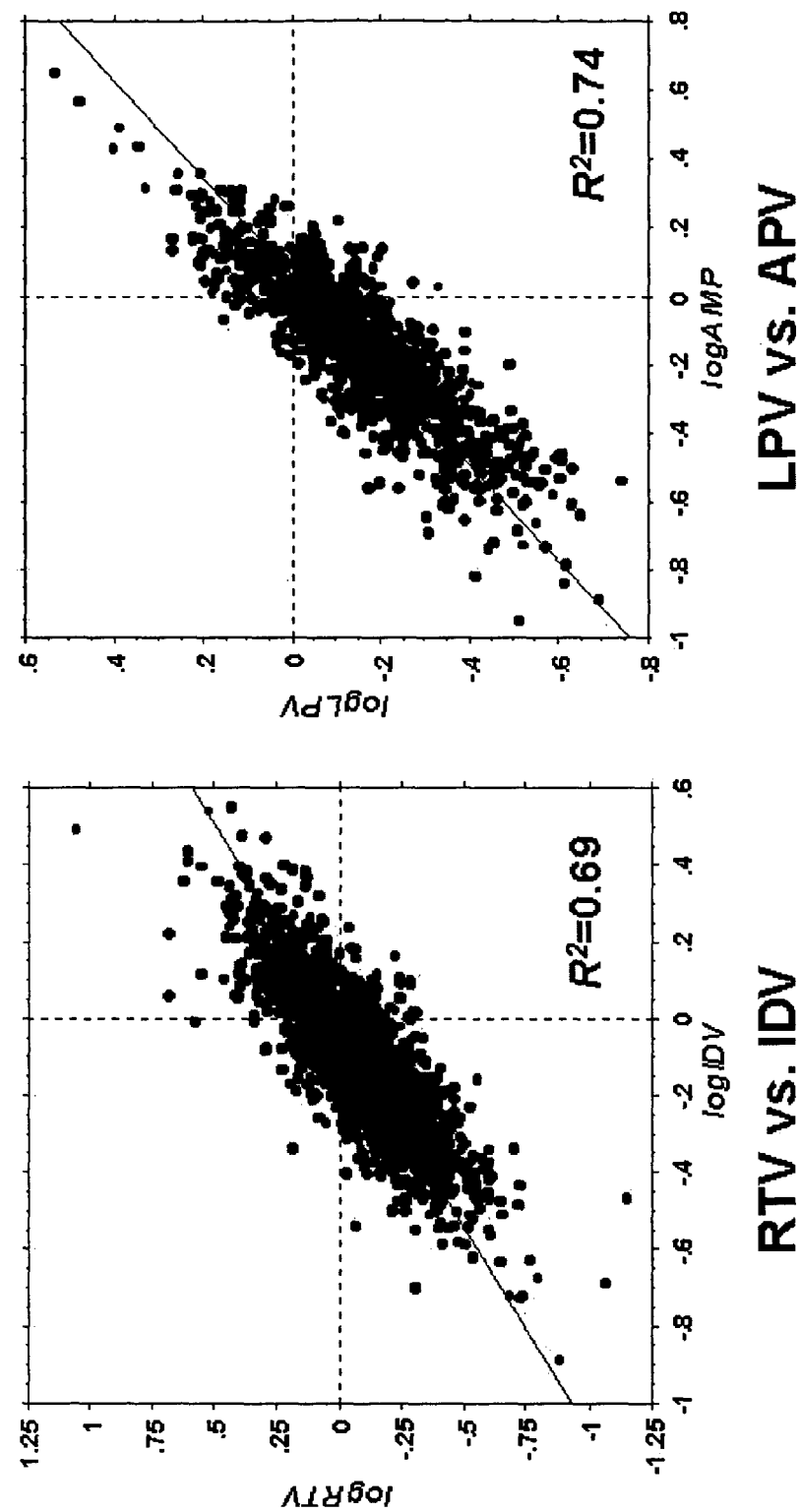
FIG. 7 shows the susceptibility co-variance of different pairs of protease inhibitors.

Effect of Mutations Associated with Hypersusceptibility to One Protease Inhibitor on Hypersusceptibility to Another Protease Inhibitor In order to confirm that the PhenoSense™ assay performance was capable of discriminating small differences in phenotypic susceptibility within the range of variability observed in the wild-type viruses, the relationship between pairs of protease inhibitors was examined. If all of the variability was due to assay performance, one would expect to find no relationship between the FC for one drug with that of another. In contrast, a close relationship was observed for many protease inhibitor pairs. Table 4 summarizes the regression coefficients for each pair. FIG. 7 shows the protease inhibitor susceptibility covariance for two pairs of protease inhibitors. As can be seen in the figure, the correlation between the protease inhibitors is very high (correlation coefficient, $R^2=0.69$ for IDV and RTV and $R^2=0.74$ for LPV and APV).

Figure 8:
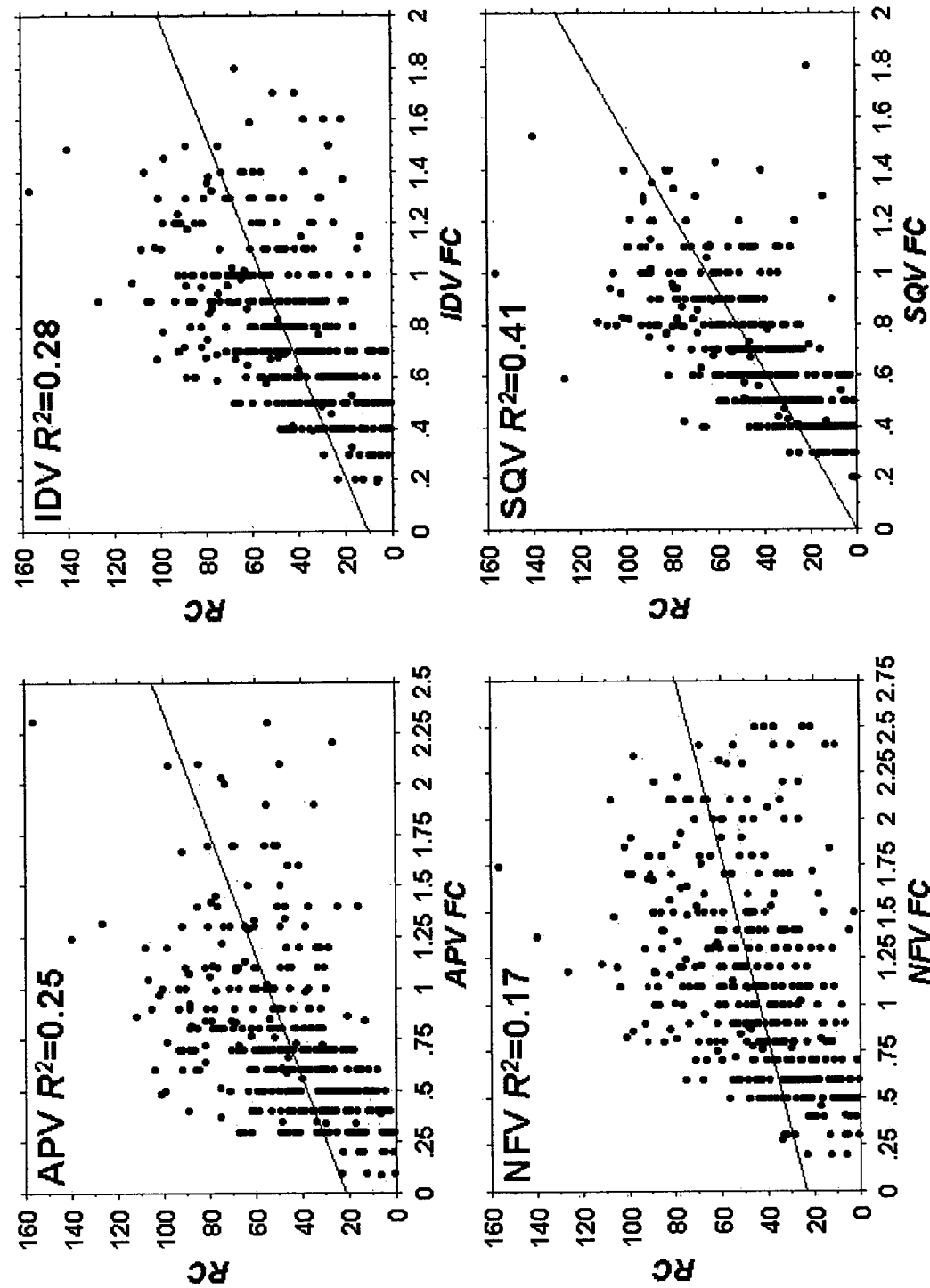
FIG. 8 shows plots of RC versus protease inhibitor FC for different protease inhibitors.

In order to determine whether hypersusceptibility to protease inhibitors was associated with reduced replication capacity ("RC") scatter plots (FIG. 8) for each protease inhibitor vs. RC was generated using a data set of 402 viruses obtained from drug-naïve, recently infected patients lacking reduced susceptibility (FC>2.5) to any drug or from a random sampling of a database sample with RC data of viruses also lacking reduced susceptibility (FC>2.5) to any drug. As can be seen in the figure, while there is a weak association for some drugs (e.g., SQV and LPV), in all cases there are many samples with low RC but normal (not HS) FC, and with high RC but HS. Thus the HS phenotype cannot always be explained by low RC.

All references cited herein are incorporated by reference in their entireties.

The examples provided herein, both actual and prophetic, are merely embodiments of the present invention and are not intended to limit the invention in any way.

TABLE 1

PROTEASE POSITIONS ASSOCIATED WITH HYPERSUSCEPTIBILITY

| Protease Inhibitor | Positive Association | Negative Association |
| --- | --- | --- |
| APV | 20, 36, 39, 65, 69, 77, 89 | 10, 15 |
| IDV | 16, 39, 65 | 10, 57, 63, 93 |
| NFV | 16, 39, 65, 69, 89 | 10, 57, 63, 71 |
| RTV | 39, 65, 93 | 15, 57 |
| SQV | 33*, 37, 45, 65, 77 | 15, 36, 41, 57, 60 |
| LPV | 33*, 39, 65, 77, 93 | none |

*all mutations at position 33, except 33F
underlined positions were associated with the largest changes in mean FC

TABLE 2

Resistance-Associated Mutations

| PROTEIN | AMINO ACID POSITIONS |
|---|---|
| PROTEASE | 23, 24, 30, 32, 33F, 46, 47, 48, 50, 54, 82 (not I), 84, 88, 90 |
| REVERSE TRANSCRIPTASE | 41, 62, 65, 67, 69, 70, 74, 75, 77, 98G, 100, 101, 103, 106, 108, 115, 116, 151, 181, 184, 188, 190, 210, 215, 219, 225, 227, 236 |

TABLE 2-continued

Resistance-Associated Mutations

| PROTEIN | AMINO ACID POSITIONS |
|---|---|

TABLE 3

DISTRIBUTION OF FOLD CHANGE VALUES

| FOLD CHANGE | APV | IDV | NFV | RTV | SQV | LPV |
|---|---|---|---|---|---|---|
| Mean | 0.69 | 0.78 | 1.05 | 0.82 | 0.70 | 0.68 |
| Median | 0.71 | 0.78 | 1.05 | 0.81 | 0.71 | 0.69 |
| $90^{th}$ Percentile | 1.32 | 1.35 | 2.09 | 1.55 | 1.12 | 1.15 |
| $10^{th}$ Percentile | 0.35 | 0.44 | 0.54 | 0.45 | 0.44 | 0.40 |

TABLE 4

Summary of Regression Coefficients for Each Pair of Protease Inhibitors

| | IDV | NFV | RTV | SQV | LPV |
|---|---|---|---|---|---|
| APV | 0.64 | 0.58 | 0.70 | 0.48 | 0.71 |
| IDV | | 0.79 | 0.68 | 0.62 | 0.71 |
| NFV | | | 0.71 | 0.49 | 0.58 |
| RTV | | | | 0.60 | 0.77 |
| SQV | | | | | 0.72 |

What is claimed is:

1. A method for determining whether an HIV-1 has an increased likelihood of being hypersusceptible to treatment with amprenavir, comprising detecting whether the protease encoded by said HIV exhibits the presence or absence of a mutation associated with hypersusceptibility to treatment with amprenavir at an amino acid position corresponding to position 39, 65, 69, or 89 of SEQ ID NO.: 1, wherein the mutation at the amino acid position corresponding to position 39 of SEQ ID NO.: 1 is S, the mutation at the amino acid position corresponding to position 65 of SEQ ID NO.: 1 is D, the mutation at the amino acid position corresponding to position 69 of SEQ ID NO.: 1 is K, and the mutation at the amino acid position corresponding to position 89 of SEQ ID NO.: 1 is M, and wherein the presence of said mutation indicates that the HIV has an increased likelihood of being hypersusceptible to treatment with amprenavir.

2. The method of claim 1, wherein the protease has a sequence that is greater than 80% identical to SEQ ID NO:1.

3. A method for determining whether an individual infected with HIV-1 has an increased likelihood of being hypersusceptible to treatment with amprenavir, comprising detecting, in a sample from said individual, the presence or absence of a mutation associated with hypersusceptibility to treatment with amprenavir at an amino acid position corresponding to position 39, 65, 69, or 89 of SEQ ID NO.: 1, wherein the mutation at the amino acid position corresponding to position 39 of SEQ ID NO.: 1 is S, the mutation at the amino acid position corresponding to position 65 of SEQ ID NO.: 1 is D, the mutation at the amino acid position corresponding to position 69 of SEQ ID NO.: 1 is K, and the mutation at the amino acid position corresponding to position 89 of SEQ ID NO.: 1 is M, and wherein the presence of said mutation indicates that the individual has an increased likelihood of being hypersusceptible to treatment with amprenavir.

4. The method of claim 3, wherein the protease has a sequence that is greater than 80% identical to SEQ ID NO:1.

5. The method of claim 3, wherein the individual is undergoing or has undergone prior treatment with an anti-viral drug.

6. The method of claim 1, wherein the method comprises detecting the presence or absence of a mutation associated with hypersusceptibility to treatment with said protease inhibitor at at least 2, 3, or 4 of the amino acid positions.

* * * * *

SEQUENCE LISTING

<160> NUMBER OF SEQ ID NOS: 2

<210> SEQ ID NO 1
<211> LENGTH: 99
<212> TYPE: PRT
<213> ORGANISM: Human immunodeficiency virus

<400> SEQUENCE: 1

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```

<210> SEQ ID NO 2
<211> LENGTH: 297
<212> TYPE: DNA
<213> ORGANISM: Human immunodeficiency virus

<400> SEQUENCE: 2

```
                                    -continued
cctcagatca ctctttggca gcgacccctc gtcacaataa agataggggg gcaattaaag       60
gaagctctat tagatacagg agcagatgat acagtattag aagaaatgaa tttgccagga      120
agatggaaac caaaaatgat aggggaatt ggaggtttta tcaaagtaag acagtatgat       180
cagatactca tagaaatctg cggacataaa gctataggta cagtattagt aggacctaca     240
cctgtcaaca taattggaag aaatctgttg actcagattg gctgcacttt aaatttt        297
```